(12) United States Patent
Hibner et al.

(10) Patent No.: US 10,959,806 B2
(45) Date of Patent: Mar. 30, 2021

(54) ENERGIZED MEDICAL DEVICE WITH REUSABLE HANDLE

(71) Applicant: Ethicon Endo-Surgery, LLC, Guaynabo, PR (US)

(72) Inventors: John A. Hibner, Mason, OH (US); Geoffrey S. Strobl, Williamsburg, OH (US); Thomas B. Remm, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 797 days.

(21) Appl. No.: 14/984,630

(22) Filed: Dec. 30, 2015

(65) Prior Publication Data
US 2017/0189102 A1 Jul. 6, 2017

(51) Int. Cl.
*A61B 18/14* (2006.01)
*A61B 90/98* (2016.01)
(Continued)

(52) U.S. Cl.
CPC .............. *A61B 90/98* (2016.02); *A61B 17/29* (2013.01); *A61B 18/1445* (2013.01);
(Continued)

(58) Field of Classification Search
CPC ..... A61B 90/03; A61B 90/98; A61B 18/1447; A61B 2017/00017; A61B 2017/00398;
(Continued)

(56) References Cited

U.S. PATENT DOCUMENTS 2,366,274 A 1/1945 Luth et al.
2,458,152 A 1/1949 Eakins
(Continued)

FOREIGN PATENT DOCUMENTS

CN 1634601 A 7/2005
CN 1640365 A 7/2005
(Continued)

OTHER PUBLICATIONS

Jang, J. et al. "Neuro-fuzzy and Soft Computing." Prentice Hall, 1997, pp. 13-89, 199-293, 335393, 453-496, 535-549.
(Continued)

*Primary Examiner* — Michael F Peffley
*Assistant Examiner* — Tigist S Demie

(57) ABSTRACT

An electrosurgical device may include a front portion releasably attached to a reusable handle. The reusable handle may include a single motor configured to actuate a tissue knife mechanism and an articulation mechanism in the front portion. The reusable handle may include a controller configured to sense a position of a knife advancement control in the front portion and actuate the tissue knife via the motor when the knife advancement control is at a predetermined position. The controller may receive data from the front portion indicating that the front portion includes an articulation joint. If the front portion includes an articulation joint, the controller may actuate, via the motor, an articulation mechanism to adjust an angle of the articulation joint when an articulation control in the front portion is at a predetermined position. The reusable handle may be used with a front portion having or lacking an articulation joint.

10 Claims, 13 Drawing Sheets

(51) Int. Cl.
*A61B 17/29* (2006.01)
*A61B 18/00* (2006.01)
*A61B 17/00* (2006.01)
*A61B 90/00* (2016.01)
*A61B 17/32* (2006.01)

(52) U.S. Cl.
CPC ... *A61B 17/2909* (2013.01); *A61B 17/320092* (2013.01); *A61B 90/03* (2016.02); *A61B 2017/003* (2013.01); *A61B 2017/00017* (2013.01); *A61B 2017/0046* (2013.01); *A61B 2017/00221* (2013.01); *A61B 2017/00327* (2013.01); *A61B 2017/00398* (2013.01); *A61B 2017/2923* (2013.01); *A61B 2017/2927* (2013.01); *A61B 2018/00196* (2013.01); *A61B 2018/00208* (2013.01); *A61B 2018/00595* (2013.01); *A61B 2018/00642* (2013.01); *A61B 2018/00922* (2013.01); *A61B 2018/1455* (2013.01)

(58) Field of Classification Search
CPC .... A61B 2017/0046; A61B 2017/2927; A61B 2018/00595; A61B 2018/00642; A61B 2018/00922; A61B 2018/1455
See application file for complete search history.

(56) References Cited

U.S. PATENT DOCUMENTS

| | | |
|---|---|---|
| 2,510,693 A | 6/1950 | Green |
| 2,736,960 A | 3/1956 | Armstrong |
| 2,849,788 A | 9/1958 | Creek |
| 2,867,039 A | 1/1959 | Zach |
| 3,015,961 A | 1/1962 | Roney |
| 3,043,309 A | 7/1962 | McCarthy |
| 3,166,971 A | 1/1965 | Stoecker |
| 3,358,676 A | 12/1967 | Frei et al. |
| 3,525,912 A | 8/1970 | Wallin |
| 3,526,219 A | 9/1970 | Balamuth |
| 3,580,841 A | 5/1971 | Cadotte et al. |
| 3,614,484 A | 10/1971 | Shoh |
| 3,636,943 A | 1/1972 | Balamuth |
| 3,703,651 A | 11/1972 | Blowers |
| 3,710,399 A | 1/1973 | Hurst |
| 3,776,238 A | 12/1973 | Peyman et al. |
| 3,777,760 A | 12/1973 | Essner |
| 3,805,787 A | 4/1974 | Banko |
| 3,862,630 A | 1/1975 | Balamuth |
| 3,900,823 A | 8/1975 | Sokal et al. |
| 3,906,217 A | 9/1975 | Lackore |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 3,988,535 A | 10/1976 | Hickman et al. |
| 4,005,714 A | 2/1977 | Hiltebrandt |
| 4,034,762 A | 7/1977 | Cosens et al. |
| 4,047,136 A | 9/1977 | Satto |
| 4,058,126 A | 11/1977 | Leveen |
| 4,063,561 A | 12/1977 | McKenna |
| 4,099,192 A | 7/1978 | Aizawa et al. |
| 4,156,187 A | 5/1979 | Murry et al. |
| 4,188,927 A | 2/1980 | Harris |
| 4,200,106 A | 4/1980 | Douvas et al. |
| 4,203,430 A | 5/1980 | Takahashi |
| 4,220,154 A | 9/1980 | Semm |
| 4,237,441 A | 12/1980 | van Konynenburg et al. |
| 4,278,077 A | 7/1981 | Mizumoto |
| 4,281,785 A | 8/1981 | Brooks |
| 4,304,987 A | 12/1981 | van Konynenburg |
| 4,314,559 A | 2/1982 | Allen |
| 4,384,584 A | 5/1983 | Chen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,585,282 A | 4/1986 | Bosley |
| 4,597,390 A | 7/1986 | Mulhollan et al. |
| 4,617,927 A | 10/1986 | Manes |
| 4,633,874 A | 1/1987 | Chow et al. |
| 4,634,420 A | 1/1987 | Spinosa et al. |
| 4,640,279 A | 2/1987 | Beard |
| 4,655,746 A | 4/1987 | Daniels et al. |
| 4,671,287 A | 6/1987 | Fiddian-Green |
| 4,708,127 A | 11/1987 | Abdelghani |
| 4,735,603 A | 4/1988 | Goodson et al. |
| 4,761,871 A | 8/1988 | O'Connor et al. |
| 4,777,951 A | 10/1988 | Cribier et al. |
| 4,797,803 A | 1/1989 | Carroll |
| 4,798,588 A | 1/1989 | Aillon |
| 4,802,461 A | 2/1989 | Cho |
| 4,803,506 A | 2/1989 | Diehl et al. |
| 4,830,462 A | 5/1989 | Karny et al. |
| 4,832,683 A | 5/1989 | Idemoto et al. |
| 4,838,853 A | 6/1989 | Parisi |
| 4,849,133 A | 7/1989 | Yoshida et al. |
| 4,850,354 A | 7/1989 | McGurk-Burleson et al. |
| 4,860,745 A | 8/1989 | Farin et al. |
| 4,865,159 A | 9/1989 | Jamison |
| 4,878,493 A | 11/1989 | Pasternak et al. |
| 4,880,015 A | 11/1989 | Nierman |
| 4,896,009 A | 1/1990 | Pawlowski |
| 4,910,389 A | 3/1990 | Sherman et al. |
| 4,910,633 A | 3/1990 | Quinn |
| 4,911,148 A | 3/1990 | Sosnowski et al. |
| 4,919,129 A | 4/1990 | Weber, Jr. et al. |
| 4,920,978 A | 5/1990 | Colvin |
| 4,922,902 A | 5/1990 | Wuchinich et al. |
| 4,936,842 A | 6/1990 | D'Amelio et al. |
| 4,961,738 A | 10/1990 | Mackin |
| 4,967,670 A | 11/1990 | Morishita et al. |
| 4,981,756 A | 1/1991 | Rhandhawa |
| 5,007,919 A | 4/1991 | Silva et al. |
| 5,019,075 A | 5/1991 | Spears et al. |
| 5,020,514 A | 6/1991 | Heckele |
| 5,026,387 A | 6/1991 | Thomas |
| 5,061,269 A | 10/1991 | Muller |
| 5,093,754 A | 3/1992 | Kawashima |
| 5,099,216 A | 3/1992 | Pelrine |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,112,300 A | 5/1992 | Ureche |
| 5,123,903 A | 6/1992 | Quaid et al. |
| 5,150,102 A | 9/1992 | Takashima |
| 5,150,272 A | 9/1992 | Danley et al. |
| 5,156,633 A | 10/1992 | Smith |
| 5,160,334 A | 11/1992 | Billings et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,188,102 A | 2/1993 | Idemoto et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,217,460 A | 6/1993 | Knoepfler |
| 5,221,282 A | 6/1993 | Wuchinich |
| 5,226,910 A | 7/1993 | Kajiyama et al. |
| 5,234,428 A | 8/1993 | Kaufman |
| 5,241,236 A | 8/1993 | Sasaki et al. |
| 5,253,647 A | 10/1993 | Takahashi et al. |
| 5,254,130 A | 10/1993 | Poncet et al. |

(56) References Cited

U.S. PATENT DOCUMENTS

| | | |
|---|---|---|
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,267,091 A | 11/1993 | Chen |
| 5,282,800 A | 2/1994 | Foshee et al. |
| 5,285,945 A | 2/1994 | Brinkerhoff et al. |
| 5,290,286 A | 3/1994 | Parins |
| 5,293,863 A | 3/1994 | Zhu et al. |
| 5,304,115 A | 4/1994 | Pflueger et al. |
| D347,474 S | 5/1994 | Olson |
| 5,309,927 A | 5/1994 | Welch |
| 5,312,023 A | 5/1994 | Green et al. |
| 5,313,306 A | 5/1994 | Kuban et al. |
| 5,318,563 A | 6/1994 | Malis et al. |
| 5,318,564 A | 6/1994 | Eggers |
| 5,318,565 A | 6/1994 | Kuriloff et al. |
| 5,318,570 A | 6/1994 | Hood et al. |
| 5,318,589 A | 6/1994 | Lichtman |
| 5,322,055 A | 6/1994 | Davison et al. |
| 5,324,260 A | 6/1994 | O'Neill et al. |
| 5,324,299 A | 6/1994 | Davison et al. |
| 5,326,013 A | 7/1994 | Green et al. |
| 5,330,471 A | 7/1994 | Eggers |
| 5,330,502 A | 7/1994 | Hassler et al. |
| 5,333,624 A | 8/1994 | Tovey |
| 5,339,723 A | 8/1994 | Huitema |
| 5,342,359 A | 8/1994 | Rydell |
| 5,344,420 A | 9/1994 | Hilal et al. |
| 5,346,502 A | 9/1994 | Estabrook et al. |
| 5,352,219 A | 10/1994 | Reddy |
| 5,359,992 A | 11/1994 | Hori et al. |
| 5,361,583 A | 11/1994 | Huitema |
| 5,366,466 A | 11/1994 | Christian et al. |
| 5,370,640 A | 12/1994 | Kolff |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,331 A | 3/1995 | O'Neill et al. |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,409,483 A | 4/1995 | Campbell et al. |
| D358,887 S | 5/1995 | Feinberg |
| 5,411,481 A | 5/1995 | Allen et al. |
| 5,413,575 A | 5/1995 | Haenggi |
| 5,417,709 A | 5/1995 | Slater |
| 5,419,761 A | 5/1995 | Narayanan et al. |
| 5,421,829 A | 6/1995 | Olichney et al. |
| 5,428,504 A | 6/1995 | Bhatla |
| 5,429,131 A | 7/1995 | Scheinman et al. |
| 5,431,640 A | 7/1995 | Gabriel |
| 5,443,463 A | 8/1995 | Stern et al. |
| 5,445,615 A | 8/1995 | Yoon |
| 5,445,638 A | 8/1995 | Rydell et al. |
| 5,449,370 A | 9/1995 | Vaitekunas |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,472,443 A | 12/1995 | Cordis et al. |
| 5,476,479 A | 12/1995 | Green et al. |
| 5,477,788 A | 12/1995 | Morishita |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,489,256 A | 2/1996 | Adair |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,648 A | 7/1996 | Yoon |
| 5,540,681 A | 7/1996 | Strul et al. |
| 5,542,916 A | 8/1996 | Hirsch et al. |
| 5,542,938 A | 8/1996 | Avellanet et al. |
| 5,558,671 A | 9/1996 | Yates |
| 5,562,609 A | 10/1996 | Brumbach |
| 5,562,610 A | 10/1996 | Brumbach |
| 5,562,657 A | 10/1996 | Griffin |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,601,601 A | 2/1997 | Tal et al. |
| 5,604,531 A | 2/1997 | Iddan et al. |
| 5,607,436 A | 3/1997 | Pratt et al. |
| 5,607,450 A | 3/1997 | Zvenyatsky et al. |
| 5,611,813 A | 3/1997 | Lichtman |
| 5,618,307 A | 4/1997 | Donlon et al. |
| 5,618,492 A | 4/1997 | Auten et al. |
| 5,624,452 A | 4/1997 | Yates |
| 5,626,578 A | 5/1997 | Tihon |
| 5,628,760 A | 5/1997 | Knoepfler |
| 5,630,420 A | 5/1997 | Vaitekunas |
| 5,632,432 A | 5/1997 | Schulze et al. |
| D381,077 S | 7/1997 | Hunt |
| 5,643,175 A | 7/1997 | Adair |
| 5,645,065 A | 7/1997 | Shapiro et al. |
| 5,647,871 A | 7/1997 | Levine et al. |
| 5,651,780 A | 7/1997 | Jackson et al. |
| 5,653,677 A | 8/1997 | Okada et al. |
| 5,653,713 A | 8/1997 | Michelson |
| 5,657,697 A | 8/1997 | Murai |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,681,260 A | 10/1997 | Ueda et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,700,243 A | 12/1997 | Narciso, Jr. |
| 5,700,261 A | 12/1997 | Brinkerhoff |
| 5,704,900 A | 1/1998 | Dobrovolny et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,722,326 A | 3/1998 | Post |
| 5,722,426 A | 3/1998 | Kolff |
| 5,732,636 A | 3/1998 | Wang et al. |
| 5,733,074 A | 3/1998 | Stock et al. |
| 5,735,848 A | 4/1998 | Yates et al. |
| 5,738,652 A | 4/1998 | Boyd et al. |
| 5,741,226 A | 4/1998 | Strukel et al. |
| 5,741,305 A | 4/1998 | Vincent et al. |
| 5,743,906 A | 4/1998 | Parins et al. |
| 5,752,973 A | 5/1998 | Kieturakis |

(56) References Cited

U.S. PATENT DOCUMENTS

| | | |
|---|---|---|
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,718 A | 9/1998 | Akiba et al. |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,828,160 A | 10/1998 | Sugishita |
| 5,836,867 A | 11/1998 | Speier et al. |
| 5,836,909 A | 11/1998 | Cosmescu |
| 5,836,943 A | 11/1998 | Miller, III |
| 5,836,990 A | 11/1998 | Li |
| 5,843,109 A | 12/1998 | Mehta et al. |
| 5,853,412 A | 12/1998 | Mayenberger |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,454 A | 3/1999 | Hones et al. |
| 5,887,018 A | 3/1999 | Bayazitoglu et al. |
| 5,891,142 A | 4/1999 | Eggers et al. |
| 5,893,835 A | 4/1999 | Witt et al. |
| 5,897,569 A | 4/1999 | Kellogg et al. |
| 5,902,239 A | 5/1999 | Buurman |
| 5,904,147 A | 5/1999 | Conlan et al. |
| 5,906,579 A | 5/1999 | Vander Salm et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,298 A | 8/1999 | Koike |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,849 A | 9/1999 | Munro |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,984,938 A | 11/1999 | Yoon |
| 5,989,182 A | 11/1999 | Hori et al. |
| 5,989,274 A | 11/1999 | Davison et al. |
| 5,989,275 A | 11/1999 | Estabrook et al. |
| 5,993,972 A | 11/1999 | Reich et al. |
| 6,003,517 A | 12/1999 | Sheffield et al. |
| 6,007,484 A | 12/1999 | Thompson |
| 6,013,052 A | 1/2000 | Durman et al. |
| 6,014,580 A | 1/2000 | Blume et al. |
| 6,024,741 A | 2/2000 | Williamson, IV et al. |
| 6,024,744 A | 2/2000 | Kese et al. |
| 6,033,375 A | 3/2000 | Brumbach |
| 6,033,399 A | 3/2000 | Gines |
| 6,039,734 A | 3/2000 | Goble |
| 6,050,996 A | 4/2000 | Schmaltz et al. |
| 6,053,172 A | 4/2000 | Hovda et al. |
| 6,063,098 A | 5/2000 | Houser et al. |
| 6,066,132 A | 5/2000 | Chen et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,152 A | 6/2000 | Nardella et al. |
| 6,083,151 A | 7/2000 | Renner et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,099,483 A | 8/2000 | Palmer et al. |
| 6,099,550 A | 8/2000 | Yoon |
| 6,109,500 A | 8/2000 | Alli et al. |
| 6,113,594 A | 9/2000 | Savage |
| 6,113,598 A | 9/2000 | Baker |
| 6,123,466 A | 9/2000 | Persson et al. |
| H1904 H | 10/2000 | Yates et al. |
| 6,127,757 A | 10/2000 | Swinbanks |
| 6,132,368 A | 10/2000 | Cooper |
| 6,139,320 A | 10/2000 | Hahn |
| 6,144,402 A | 11/2000 | Norsworthy et al. |
| 6,152,902 A | 11/2000 | Christian et al. |
| 6,152,923 A | 11/2000 | Ryan |
| 6,154,198 A | 11/2000 | Rosenberg |
| 6,159,160 A | 12/2000 | Hsei et al. |
| 6,159,175 A | 12/2000 | Strukel et al. |
| 6,162,208 A | 12/2000 | Hipps |
| 6,173,199 B1 | 1/2001 | Gabriel |
| 6,173,715 B1 | 1/2001 | Sinanan et al. |
| 6,174,309 B1 | 1/2001 | Wrublewski et al. |
| 6,176,857 B1 | 1/2001 | Ashley |
| 6,190,386 B1 | 2/2001 | Rydell |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,403 B1 | 4/2001 | Klicek |
| 6,214,023 B1 | 4/2001 | Whipple et al. |
| 6,219,572 B1 | 4/2001 | Young |
| 6,221,007 B1 | 4/2001 | Green |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,248,074 B1 | 6/2001 | Ohno et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,258,086 B1 | 7/2001 | Ashley et al. |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,273,887 B1 | 8/2001 | Yamauchi et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,283,981 B1 | 9/2001 | Beaupre |
| 6,292,700 B1 | 9/2001 | Morrison et al. |
| 6,309,400 B2 | 10/2001 | Beaupre |
| 6,315,789 B1 | 11/2001 | Cragg |
| 6,319,221 B1 | 11/2001 | Savage et al. |
| 6,325,799 B1 | 12/2001 | Goble |
| 6,325,811 B1 | 12/2001 | Messerly |
| 6,328,751 B1 | 12/2001 | Beaupre |
| 6,340,878 B1 | 1/2002 | Oglesbee |
| 6,352,532 B1 | 3/2002 | Kramer et al. |
| 6,364,888 B1 | 4/2002 | Niemeyer et al. |
| 6,371,952 B1 | 4/2002 | Madhani et al. |
| 6,379,320 B1 | 4/2002 | Lafon et al. |
| D457,958 S | 5/2002 | Dycus et al. |
| 6,383,194 B1 | 5/2002 | Pothula |
| 6,387,094 B1 | 5/2002 | Eitenmuller |
| 6,387,109 B1 | 5/2002 | Davison et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |

(56) References Cited

U.S. PATENT DOCUMENTS

| | | |
|---|---|---|
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,443,968 B1 | 9/2002 | Holthaus et al. |
| 6,443,969 B1 | 9/2002 | Novak et al. |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,464,703 B2 | 10/2002 | Bartel |
| 6,471,172 B1 | 10/2002 | Lemke et al. |
| 6,475,211 B2 | 11/2002 | Chess et al. |
| 6,475,216 B2 | 11/2002 | Mulier et al. |
| 6,480,796 B2 | 11/2002 | Wiener |
| 6,485,490 B2 | 11/2002 | Wampler et al. |
| 6,491,690 B1 | 12/2002 | Goble et al. |
| 6,491,691 B1 | 12/2002 | Morley et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,520,960 B2 | 2/2003 | Blocher et al. |
| 6,522,909 B1 | 2/2003 | Garibaldi et al. |
| 6,524,316 B1 | 2/2003 | Nicholson et al. |
| 6,531,846 B1 | 3/2003 | Smith |
| 6,533,784 B2 | 3/2003 | Truckai et al. |
| 6,537,196 B1 | 3/2003 | Creighton, IV et al. |
| 6,537,272 B2 | 3/2003 | Christopherson et al. |
| 6,537,291 B2 | 3/2003 | Friedman et al. |
| 6,540,693 B2 | 4/2003 | Burbank et al. |
| 6,543,456 B2 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,037 B2 | 5/2003 | Paton et al. |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,589,239 B2 | 7/2003 | Khandkar et al. |
| 6,594,517 B1 | 7/2003 | Nevo |
| 6,599,321 B2 | 7/2003 | Hyde, Jr. |
| 6,602,252 B2 | 8/2003 | Mollenauer |
| 6,610,060 B2 | 8/2003 | Mulier et al. |
| 6,616,450 B2 | 9/2003 | Mossle et al. |
| 6,616,600 B2 | 9/2003 | Pauker |
| 6,619,529 B2 | 9/2003 | Green et al. |
| 6,620,129 B2 | 9/2003 | Stecker et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,817 B2 | 11/2003 | Schara et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,663,941 B2 | 12/2003 | Brown et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,695,840 B2 | 2/2004 | Schulze |
| 6,716,215 B1 | 4/2004 | David et al. |
| 6,719,684 B2 | 4/2004 | Kim et al. |
| 6,719,765 B2 | 4/2004 | Bonutti |
| 6,722,552 B2 | 4/2004 | Fenton, Jr. |
| 6,726,686 B2 | 4/2004 | Buysse et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,743,229 B2 | 6/2004 | Buysse et al. |
| 6,746,443 B1 | 6/2004 | Morley et al. |
| 6,752,815 B2 | 6/2004 | Beaupre |
| 6,762,535 B2 | 7/2004 | Take et al. |
| 6,766,202 B2 | 7/2004 | Underwood et al. |
| 6,767,349 B2 | 7/2004 | Ouchi |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,165 B2 | 8/2004 | Jin |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,216 B1 | 9/2004 | Ishikawa |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,806,317 B2 | 10/2004 | Morishita et al. |
| 6,808,491 B2 | 10/2004 | Kortenbach et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,828,712 B2 | 12/2004 | Battaglin et al. |
| 6,832,998 B2 | 12/2004 | Goble |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,869,439 B2 | 3/2005 | White et al. |
| 6,875,220 B2 | 4/2005 | Du et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,632 B2 | 8/2005 | Nita et al. |
| 6,929,644 B2 | 8/2005 | Truckai et al. |
| 6,936,003 B2 | 8/2005 | Iddan |
| D509,589 S | 9/2005 | Wells |
| 6,939,347 B2 | 9/2005 | Thompson |
| 6,945,981 B2 | 9/2005 | Donofrio et al. |
| 6,953,461 B2 | 10/2005 | McClurken et al. |
| D511,145 S | 11/2005 | Donofrio et al. |

(56) References Cited

U.S. PATENT DOCUMENTS

| | | |
|---|---|---|
| 6,959,852 B2 | 11/2005 | Shelton, IV et al. |
| 6,974,462 B2 | 12/2005 | Sater |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 6,986,738 B2 | 1/2006 | Glukhovsky et al. |
| 6,986,780 B2 | 1/2006 | Rudnick et al. |
| 6,994,709 B2 | 2/2006 | Iida |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,029,435 B2 | 4/2006 | Nakao |
| 7,039,453 B2 | 5/2006 | Mullick et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,352 B2 | 5/2006 | Shelton, IV et al. |
| 7,044,937 B1 | 5/2006 | Kirwan et al. |
| 7,052,496 B2 | 5/2006 | Yamauchi |
| 7,055,731 B2 | 6/2006 | Shelton, IV et al. |
| 7,056,284 B2 | 6/2006 | Martone et al. |
| 7,063,699 B2 | 6/2006 | Hess et al. |
| 7,066,879 B2 | 6/2006 | Fowler et al. |
| 7,066,936 B2 | 6/2006 | Ryan |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,579 B2 | 8/2006 | Yokoi et al. |
| 7,083,617 B2 | 8/2006 | Kortenbach et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,094,235 B2 | 8/2006 | Francischelli |
| 7,096,560 B2 | 8/2006 | Oddsen, Jr. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,118,570 B2 | 10/2006 | Tetzlaff et al. |
| 7,120,498 B2 | 10/2006 | Imran et al. |
| 7,124,932 B2 | 10/2006 | Isaacson et al. |
| 7,125,409 B2 | 10/2006 | Truckai et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,147,638 B2 | 12/2006 | Chapman et al. |
| 7,153,315 B2 | 12/2006 | Miller |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,163,548 B2 | 1/2007 | Stulen et al. |
| 7,169,104 B2 | 1/2007 | Ueda et al. |
| 7,169,146 B2 | 1/2007 | Truckai et al. |
| 7,169,156 B2 | 1/2007 | Hart |
| 7,170,823 B2 | 1/2007 | Fabricius et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,199,545 B2 | 4/2007 | Oleynikov et al. |
| 7,204,820 B2 | 4/2007 | Akahoshi |
| 7,207,471 B2 | 4/2007 | Heinrich et al. |
| 7,208,005 B2 | 4/2007 | Frecker et al. |
| 7,211,094 B2 | 5/2007 | Gannoe et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,064 B2 | 6/2007 | Hopper et al. |
| 7,235,073 B2 | 6/2007 | Levine et al. |
| 7,241,290 B2 | 7/2007 | Doyle et al. |
| 7,241,294 B2 | 7/2007 | Reschke |
| 7,241,296 B2 | 7/2007 | Buysse et al. |
| 7,246,734 B2 | 7/2007 | Shelton, IV |
| 7,251,531 B2 | 7/2007 | Mosher et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,267,685 B2 | 9/2007 | Butaric et al. |
| 7,270,664 B2 | 9/2007 | Johnson et al. |
| 7,273,483 B2 | 9/2007 | Wiener et al. |
| 7,276,065 B2 | 10/2007 | Morley et al. |
| 7,282,773 B2 | 10/2007 | Li et al. |
| 7,287,682 B1 | 10/2007 | Ezzat et al. |
| 7,297,145 B2 | 11/2007 | Woloszko et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,360,542 B2 | 4/2008 | Nelson et al. |
| 7,364,577 B2 | 4/2008 | Wham et al. |
| 7,367,973 B2 | 5/2008 | Manzo et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| D576,725 S | 9/2008 | Shumer et al. |
| 7,422,139 B2 | 9/2008 | Shelton, IV et al. |
| 7,422,586 B2 | 9/2008 | Morris et al. |
| 7,422,592 B2 | 9/2008 | Morley et al. |
| 7,429,259 B2 | 9/2008 | Cadeddu et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,249 B2 | 10/2008 | Buysse et al. |
| 7,435,582 B2 | 10/2008 | Zimmermann et al. |
| 7,439,732 B2 | 10/2008 | LaPlaca |
| 7,441,684 B2 | 10/2008 | Shelton, IV et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,448,993 B2 | 11/2008 | Yokoi et al. |
| 7,449,004 B2 | 11/2008 | Yamada et al. |
| 7,450,998 B2 | 11/2008 | Zilberman et al. |
| 7,451,904 B2 | 11/2008 | Shelton, IV |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,479,148 B2 | 1/2009 | Beaupre |

(56) References Cited

U.S. PATENT DOCUMENTS

| | | |
|---|---|---|
| 7,479,160 B2 | 1/2009 | Branch et al. |
| 7,487,899 B2 | 2/2009 | Shelton, IV et al. |
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,503,893 B2 | 3/2009 | Kucklick |
| 7,505,812 B1 | 3/2009 | Eggers et al. |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,511,733 B2 | 3/2009 | Takizawa et al. |
| 7,513,025 B2 | 4/2009 | Fischer |
| 7,517,349 B2 | 4/2009 | Truckai et al. |
| 7,520,877 B2 | 4/2009 | Lee, Jr. et al. |
| 7,524,320 B2 | 4/2009 | Tierney et al. |
| 7,534,243 B1 | 5/2009 | Chin et al. |
| D594,983 S | 6/2009 | Price et al. |
| 7,540,872 B2 | 6/2009 | Schechter et al. |
| 7,543,730 B1 | 6/2009 | Marczyk |
| 7,544,200 B2 | 6/2009 | Houser |
| 7,550,216 B2 | 6/2009 | Ofer et al. |
| 7,553,309 B2 | 6/2009 | Buysse et al. |
| 7,559,452 B2 | 7/2009 | Wales et al. |
| 7,566,318 B2 | 7/2009 | Haefner |
| 7,567,012 B2 | 7/2009 | Namikawa |
| 7,582,086 B2 | 9/2009 | Privitera et al. |
| 7,582,087 B2 | 9/2009 | Tetzlaff et al. |
| 7,586,289 B2 | 9/2009 | Andruk et al. |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,599,743 B2 | 10/2009 | Hassler, Jr. et al. |
| 7,601,119 B2 | 10/2009 | Shahinian |
| 7,604,150 B2 | 10/2009 | Boudreaux |
| 7,611,512 B2 | 11/2009 | Ein-Gal |
| 7,617,961 B2 | 11/2009 | Viola |
| 7,621,910 B2 | 11/2009 | Sugi |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,640,447 B2 | 12/2009 | Qiu |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,678,043 B2 | 3/2010 | Gilad |
| 7,678,105 B2 | 3/2010 | McGreevy et al. |
| 7,686,804 B2 | 3/2010 | Johnson et al. |
| 7,691,095 B2 | 4/2010 | Bednarek et al. |
| 7,691,098 B2 | 4/2010 | Wallace et al. |
| 7,691,103 B2 | 4/2010 | Fernandez et al. |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,717,312 B2 | 5/2010 | Beetel |
| 7,717,914 B2 | 5/2010 | Kimura |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,725,214 B2 | 5/2010 | Diolaiti |
| D618,797 S | 6/2010 | Price et al. |
| 7,726,537 B2 | 6/2010 | Olson et al. |
| 7,744,615 B2 | 6/2010 | Couture |
| 7,751,115 B2 | 7/2010 | Song |
| 7,753,904 B2 | 7/2010 | Shelton, IV et al. |
| 7,753,908 B2 | 7/2010 | Swanson |
| 7,753,909 B2 | 7/2010 | Chapman et al. |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,775,972 B2 | 8/2010 | Brock et al. |
| 7,776,036 B2 | 8/2010 | Schechter et al. |
| 7,776,037 B2 | 8/2010 | Odom |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,663 B2 | 8/2010 | Shelton, IV |
| 7,789,283 B2 | 9/2010 | Shah |
| 7,789,878 B2 | 9/2010 | Dumbauld et al. |
| 7,789,883 B2 | 9/2010 | Takashino et al. |
| 7,793,814 B2 | 9/2010 | Racenet et al. |
| 7,799,027 B2 | 9/2010 | Hafner |
| 7,803,156 B2 | 9/2010 | Eder et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| D627,066 S | 11/2010 | Romero |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,837,699 B2 | 11/2010 | Yamada et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,850,688 B2 | 12/2010 | Hafner |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| D631,965 S | 2/2011 | Price et al. |
| 7,877,852 B2 | 2/2011 | Unger et al. |
| 7,877,853 B2 | 2/2011 | Unger et al. |
| 7,879,035 B2 | 2/2011 | Garrison et al. |
| 7,879,070 B2 | 2/2011 | Ortiz et al. |
| 7,892,606 B2 | 2/2011 | Thies et al. |
| 7,896,875 B2 | 3/2011 | Heim et al. |
| 7,896,878 B2 | 3/2011 | Johnson et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,953 B2 | 4/2011 | Guerra |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,942,303 B2 | 5/2011 | Shah |
| 7,942,868 B2 | 5/2011 | Cooper |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,976,544 B2 | 7/2011 | McClurken et al. |
| 7,980,443 B2 | 7/2011 | Scheib et al. |
| 7,981,113 B2 | 7/2011 | Truckai et al. |

(56) References Cited

U.S. PATENT DOCUMENTS

| | | |
|---|---|---|
| 7,988,567 B2 | 8/2011 | Kim et al. |
| 7,997,278 B2 | 8/2011 | Utley et al. |
| 8,020,743 B2 | 9/2011 | Shelton, IV |
| 8,033,173 B2 | 10/2011 | Ehlert et al. |
| 8,038,612 B2 | 10/2011 | Paz |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,056,787 B2 | 11/2011 | Boudreaux et al. |
| 8,057,498 B2 | 11/2011 | Robertson |
| 8,058,771 B2 | 11/2011 | Giordano et al. |
| 8,061,014 B2 | 11/2011 | Smith et al. |
| 8,062,211 B2 | 11/2011 | Duval et al. |
| 8,066,167 B2 | 11/2011 | Measamer et al. |
| 8,070,036 B1 | 12/2011 | Knodel |
| 8,070,748 B2 | 12/2011 | Hixson et al. |
| 8,075,555 B2 | 12/2011 | Truckai et al. |
| 8,075,558 B2 | 12/2011 | Truckai et al. |
| 8,092,475 B2 | 1/2012 | Cotter et al. |
| 8,100,894 B2 | 1/2012 | Mucko et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,114,119 B2 | 2/2012 | Spivey et al. |
| 8,128,624 B2 | 3/2012 | Couture et al. |
| 8,128,657 B2 | 3/2012 | Shiono et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,177,794 B2 | 5/2012 | Cabrera et al. |
| 8,182,502 B2 | 5/2012 | Stulen et al. |
| 8,186,560 B2 | 5/2012 | Hess et al. |
| 8,187,166 B2 | 5/2012 | Kuth et al. |
| 8,187,267 B2 | 5/2012 | Pappone et al. |
| 8,192,433 B2 | 6/2012 | Johnson et al. |
| 8,197,472 B2 | 6/2012 | Lau et al. |
| 8,197,479 B2 | 6/2012 | Olson et al. |
| 8,197,494 B2 | 6/2012 | Jaggi et al. |
| 8,197,502 B2 | 6/2012 | Smith et al. |
| 8,206,212 B2 | 6/2012 | Iddings et al. |
| 8,221,415 B2 | 7/2012 | Francischelli |
| 8,226,675 B2 | 7/2012 | Houser et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,244,368 B2 | 8/2012 | Sherman |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,257,352 B2 | 9/2012 | Lawes et al. |
| 8,257,377 B2 | 9/2012 | Wiener et al. |
| 8,262,563 B2 | 9/2012 | Bakos et al. |
| 8,267,300 B2 | 9/2012 | Boudreaux |
| 8,267,854 B2 | 9/2012 | Asada et al. |
| 8,267,935 B2 | 9/2012 | Couture et al. |
| 8,273,085 B2 | 9/2012 | Park et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,228 B2 | 10/2012 | Buysse et al. |
| 8,298,232 B2 | 10/2012 | Unger |
| 8,303,583 B2 | 11/2012 | Hosier et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,322,455 B2 | 12/2012 | Shelton, IV et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,053 B2 | 2/2013 | Orszulak |
| 8,377,059 B2 | 2/2013 | Deville et al. |
| 8,377,085 B2 | 2/2013 | Smith et al. |
| 8,382,754 B2 | 2/2013 | Odom et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,094 B2 | 3/2013 | Edwards et al. |
| 8,394,115 B2 | 3/2013 | Houser et al. |
| 8,397,971 B2 | 3/2013 | Yates et al. |
| 8,403,926 B2 | 3/2013 | Nobis et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,076 B2 | 4/2013 | Pang et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,956 B2 | 6/2013 | McKenna et al. |
| 8,469,981 B2 | 6/2013 | Robertson et al. |
| 8,475,361 B2 | 7/2013 | Barlow et al. |
| 8,475,453 B2 | 7/2013 | Marczyk et al. |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,625 B2 | 7/2013 | Homer |
| 8,496,682 B2 | 7/2013 | Guerra et al. |
| 8,512,336 B2 | 8/2013 | Couture |

(56) References Cited

U.S. PATENT DOCUMENTS

| | | |
|---|---|---|
| 8,512,364 B2 | 8/2013 | Kowalski et al. |
| 8,512,365 B2 | 8/2013 | Wiener et al. |
| 8,523,889 B2 | 9/2013 | Stulen et al. |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,542,501 B2 | 9/2013 | Kyono |
| 8,553,430 B2 | 10/2013 | Melanson et al. |
| 8,562,516 B2 | 10/2013 | Saadat et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,187 B2 | 11/2013 | Marion |
| 8,574,231 B2 | 11/2013 | Boudreaux et al. |
| 8,579,176 B2 | 11/2013 | Smith et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| D695,407 S | 12/2013 | Price et al. |
| 8,596,513 B2 | 12/2013 | Olson et al. |
| 8,597,182 B2 | 12/2013 | Stein et al. |
| 8,597,297 B2 | 12/2013 | Couture et al. |
| 8,608,044 B2 | 12/2013 | Hueil et al. |
| 8,613,383 B2 | 12/2013 | Beckman et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,632,539 B2 | 1/2014 | Twomey et al. |
| 8,636,648 B2 | 1/2014 | Gazdzinski |
| 8,636,736 B2 | 1/2014 | Yates et al. |
| 8,636,761 B2 | 1/2014 | Cunningham et al. |
| 8,638,428 B2 | 1/2014 | Brown |
| 8,640,788 B2 | 2/2014 | Dachs, II et al. |
| 8,641,712 B2 | 2/2014 | Couture |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,668,691 B2 | 3/2014 | Heard |
| RE44,834 E | 4/2014 | Dumbauld et al. |
| 8,684,253 B2 | 4/2014 | Giordano et al. |
| 8,685,020 B2 | 4/2014 | Weizman et al. |
| 8,685,056 B2 | 4/2014 | Evans et al. |
| 8,696,662 B2 | 4/2014 | Eder et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,708,213 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,770,459 B2 | 7/2014 | Racenet et al. |
| 8,784,418 B2 | 7/2014 | Romero |
| 8,789,740 B2 | 7/2014 | Baxter, III et al. |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,752 B2 | 8/2014 | Fortier et al. |
| 8,808,319 B2 | 8/2014 | Houser et al. |
| 8,814,856 B2 | 8/2014 | Elmouelhi et al. |
| 8,814,865 B2 | 8/2014 | Reschke |
| 8,814,870 B2 | 8/2014 | Paraschiv et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,488 B2 | 9/2014 | Farritor et al. |
| 8,834,518 B2 | 9/2014 | Faller et al. |
| 8,845,630 B2 | 9/2014 | Mehta et al. |
| 8,851,354 B2 | 10/2014 | Swensgard et al. |
| 8,852,184 B2 | 10/2014 | Kucklick |
| 8,864,757 B2 | 10/2014 | Klimovitch et al. |
| 8,864,761 B2 | 10/2014 | Johnson et al. |
| 8,870,867 B2 | 10/2014 | Walberg et al. |
| 8,876,858 B2 | 11/2014 | Braun |
| 8,882,766 B2 | 11/2014 | Couture et al. |
| 8,882,791 B2 | 11/2014 | Stulen |
| 8,887,373 B2 | 11/2014 | Brandt et al. |
| 8,888,776 B2 | 11/2014 | Dietz et al. |
| 8,888,783 B2 | 11/2014 | Young |
| 8,888,809 B2 | 11/2014 | Davison et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,926,607 B2 | 1/2015 | Norvell et al. |
| 8,926,608 B2 | 1/2015 | Bacher et al. |
| 8,929,888 B2 | 1/2015 | Rao et al. |
| 8,931,682 B2 | 1/2015 | Timm et al. |
| 8,939,287 B2 | 1/2015 | Markovitch |
| 8,939,974 B2 | 1/2015 | Boudreaux et al. |
| 8,939,975 B2 | 1/2015 | Twomey et al. |
| 8,944,997 B2 | 2/2015 | Fernandez et al. |
| 8,945,125 B2 | 2/2015 | Schechter et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,968,276 B2 | 3/2015 | Zemlok et al. |
| 8,968,308 B2 | 3/2015 | Homer et al. |
| 8,968,312 B2 | 3/2015 | Marczyk et al. |
| 8,968,332 B2 | 3/2015 | Farritor et al. |
| 8,978,845 B2 | 3/2015 | Kim |
| 8,979,838 B2 | 3/2015 | Woloszko et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,989,855 B2 | 3/2015 | Murphy et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,372 B2 | 4/2015 | Artale et al. |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,983 B2 | 5/2015 | Takashino et al. |
| 9,039,695 B2 | 5/2015 | Giordano et al. |
| 9,039,705 B2 | 5/2015 | Takashino |
| 9,039,731 B2 | 5/2015 | Joseph |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |

(56) References Cited

U.S. PATENT DOCUMENTS

| | | |
|---|---|---|
| 9,050,093 B2 | 6/2015 | Aldridge et al. |
| 9,050,098 B2 | 6/2015 | Deville et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,078,664 B2 | 7/2015 | Palmer et al. |
| 9,089,327 B2 | 7/2015 | Worrell et al. |
| 9,089,360 B2 | 7/2015 | Messerly et al. |
| 9,094,006 B2 | 7/2015 | Gravati et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,672 B2 | 8/2015 | Tetzlaff et al. |
| 9,113,889 B2 | 8/2015 | Reschke |
| 9,113,900 B2 | 8/2015 | Buysse et al. |
| 9,119,630 B2 | 9/2015 | Townsend et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,138,289 B2 | 9/2015 | Conley et al. |
| 9,149,324 B2 | 10/2015 | Huang et al. |
| 9,149,325 B2 | 10/2015 | Worrell et al. |
| 9,155,585 B2 | 10/2015 | Bales, Jr. et al. |
| 9,161,803 B2 | 10/2015 | Yates et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,179,912 B2 | 11/2015 | Yates et al. |
| 9,186,204 B2 | 11/2015 | Nishimura et al. |
| 9,187,758 B2 | 11/2015 | Cai et al. |
| 9,192,380 B2 | 11/2015 | (Tarinelli) Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,716 B2 | 12/2015 | Masuda et al. |
| 9,204,879 B2 | 12/2015 | Shelton, IV |
| 9,204,919 B2 | 12/2015 | Brandt et al. |
| 9,216,050 B2 | 12/2015 | Condie et al. |
| 9,220,559 B2 | 12/2015 | Worrell et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,571 B2 | 2/2016 | Twomey et al. |
| 9,265,926 B2 | 2/2016 | Strobl et al. |
| 9,271,784 B2 | 3/2016 | Evans et al. |
| 9,274,988 B2 | 3/2016 | Hsu et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,326,788 B2 | 5/2016 | Batross et al. |
| 9,333,025 B2 | 5/2016 | Monson et al. |
| 9,339,323 B2 | 5/2016 | Eder et al. |
| 9,339,326 B2 | 5/2016 | McCullagh et al. |
| 9,344,042 B2 | 5/2016 | Mao |
| 9,345,481 B2 | 5/2016 | Hall et al. |
| 9,345,900 B2 | 5/2016 | Wu et al. |
| 9,351,754 B2 | 5/2016 | Vakharia et al. |
| 9,358,065 B2 | 6/2016 | Ladtkow et al. |
| 9,364,230 B2 | 6/2016 | Shelton, IV et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,381,060 B2 | 7/2016 | Artale et al. |
| 9,386,983 B2 | 7/2016 | Swensgard et al. |
| 9,393,037 B2 | 7/2016 | Olson et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,456,876 B2 | 10/2016 | Hagn |
| 9,492,224 B2 | 11/2016 | Boudreaux et al. |
| 9,504,524 B2 | 11/2016 | Behnke, II |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,549,663 B2 | 1/2017 | Larkin |
| 9,554,845 B2 | 1/2017 | Arts |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,585,709 B2 | 3/2017 | Krapohl |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,810 B2 | 4/2017 | Hart et al. |
| 9,627,120 B2 | 4/2017 | Scott et al. |
| 9,629,629 B2 | 4/2017 | Leimbach et al. |
| 9,642,669 B2 | 5/2017 | Takashino et al. |
| 9,649,111 B2 | 5/2017 | Shelton, IV et al. |
| 9,649,144 B2 | 5/2017 | Aluru et al. |
| 9,649,151 B2 | 5/2017 | Goodman et al. |
| 9,662,131 B2 | 5/2017 | Omori et al. |
| 9,668,806 B2 | 6/2017 | Unger et al. |
| 9,687,295 B2 | 6/2017 | Joseph |
| 9,700,339 B2 | 7/2017 | Nield |
| 9,707,005 B2 | 7/2017 | Strobl et al. |
| 9,707,027 B2 | 7/2017 | Ruddenklau et al. |
| 9,707,030 B2 | 7/2017 | Davison et al. |
| 9,713,491 B2 | 7/2017 | Roy et al. |
| 9,724,118 B2 | 8/2017 | Schulte et al. |
| 9,724,152 B2 | 8/2017 | Horlle et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,757,128 B2 | 9/2017 | Baber et al. |
| 9,757,142 B2 | 9/2017 | Shimizu |
| 9,757,186 B2 | 9/2017 | Boudreaux et al. |
| 9,782,214 B2 | 10/2017 | Houser et al. |
| 9,782,220 B2 | 10/2017 | Mark et al. |
| 9,795,436 B2 | 10/2017 | Yates et al. |
| 9,802,033 B2 | 10/2017 | Hibner et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,833,239 B2 | 12/2017 | Yates et al. |
| 9,848,937 B2 | 12/2017 | Trees et al. |
| 9,848,939 B2 | 12/2017 | Mayer et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,877,782 B2 | 1/2018 | Voegele et al. |
| 9,888,958 B2 | 2/2018 | Evans et al. |
| 9,901,390 B2 | 2/2018 | Allen, IV et al. |
| 9,901,754 B2 | 2/2018 | Yamada |
| 9,907,563 B2 | 3/2018 | Germain et al. |
| 9,913,680 B2 | 3/2018 | Voegele et al. |
| 9,918,730 B2 | 3/2018 | Trees et al. |
| 9,931,157 B2 | 4/2018 | Strobl et al. |
| 9,937,001 B2 | 4/2018 | Nakamura |
| 9,943,357 B2 | 4/2018 | Cunningham et al. |

(56) References Cited

U.S. PATENT DOCUMENTS

| | | |
|---|---|---|
| 9,949,620 B2 | 4/2018 | Duval et al. |
| 9,949,785 B2 | 4/2018 | Price et al. |
| 9,949,788 B2 | 4/2018 | Boudreaux |
| 9,974,539 B2 | 5/2018 | Yates et al. |
| 9,993,289 B2 | 6/2018 | Sobajima et al. |
| 10,010,339 B2 | 7/2018 | Witt et al. |
| 10,016,207 B2 | 7/2018 | Suzuki et al. |
| 10,022,142 B2 | 7/2018 | Aranyi et al. |
| 10,041,822 B2 | 8/2018 | Zemlok |
| 10,052,044 B2 | 8/2018 | Shelton, IV et al. |
| 10,058,376 B2 | 8/2018 | Horner et al. |
| 10,070,916 B2 | 9/2018 | Artale |
| 10,080,606 B2 | 9/2018 | Kappus et al. |
| 10,092,310 B2 | 10/2018 | Boudreaux et al. |
| 10,092,348 B2 | 10/2018 | Boudreaux |
| 10,092,350 B2 | 10/2018 | Rothweiler et al. |
| 10,105,174 B2 | 10/2018 | Krapohl |
| 10,111,699 B2 | 10/2018 | Boudreaux |
| 10,117,702 B2 | 11/2018 | Danziger et al. |
| 10,130,410 B2 | 11/2018 | Strobl et al. |
| 10,130,414 B2 | 11/2018 | Weiler et al. |
| 10,194,911 B2 | 2/2019 | Miller et al. |
| 10,211,586 B2 | 2/2019 | Adams et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0077550 A1 | 6/2002 | Rabiner et al. |
| 2002/0095175 A1 | 7/2002 | Brock et al. |
| 2002/0107517 A1 | 8/2002 | Witt et al. |
| 2002/0156493 A1 | 10/2002 | Houser et al. |
| 2003/0014053 A1 | 1/2003 | Nguyen et al. |
| 2003/0055443 A1 | 3/2003 | Spotnitz |
| 2003/0066938 A1 | 4/2003 | Zimmerman |
| 2003/0109875 A1 | 6/2003 | Tetzlaff et al. |
| 2003/0114731 A1 | 6/2003 | Cadeddu et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0204199 A1 | 10/2003 | Novak et al. |
| 2003/0212332 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0092992 A1 | 5/2004 | Adams et al. |
| 2004/0093039 A1 | 5/2004 | Schumert |
| 2004/0097919 A1 | 5/2004 | Wellman et al. |
| 2004/0097996 A1 | 5/2004 | Rabiner et al. |
| 2004/0102804 A1 | 5/2004 | Chin |
| 2004/0133089 A1 | 7/2004 | Kilcoyne et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0199193 A1 | 10/2004 | Hayashi et al. |
| 2004/0249367 A1 | 12/2004 | Saadat et al. |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0033278 A1 | 2/2005 | McClurken et al. |
| 2005/0033337 A1 | 2/2005 | Muir et al. |
| 2005/0090817 A1 | 4/2005 | Phan |
| 2005/0096502 A1 | 5/2005 | Khalili |
| 2005/0119640 A1 | 6/2005 | Sverduk et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0192610 A1 | 9/2005 | Houser et al. |
| 2005/0215858 A1 | 9/2005 | Vail |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0272972 A1 | 12/2005 | Iddan |
| 2005/0273139 A1 | 12/2005 | Krauss et al. |
| 2005/0288555 A1 | 12/2005 | Binmoeller |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0159731 A1 | 7/2006 | Shoshan |
| 2006/0190034 A1 | 8/2006 | Nishizawa et al. |
| 2006/0211943 A1 | 9/2006 | Beaupre |
| 2006/0253050 A1 | 11/2006 | Yoshimine et al. |
| 2006/0270916 A1 | 11/2006 | Skwarek et al. |
| 2006/0293656 A1 | 12/2006 | Shadduck et al. |
| 2007/0008744 A1 | 1/2007 | Heo et al. |
| 2007/0010709 A1 | 1/2007 | Reinschke |
| 2007/0016235 A1 | 1/2007 | Tanaka et al. |
| 2007/0016236 A1 | 1/2007 | Beaupre |
| 2007/0020065 A1 | 1/2007 | Kirby |
| 2007/0032701 A1 | 2/2007 | Fowler et al. |
| 2007/0032704 A1 | 2/2007 | Gandini et al. |
| 2007/0051766 A1 | 3/2007 | Spencer |
| 2007/0055228 A1 | 3/2007 | Berg et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0106317 A1 | 5/2007 | Shelton et al. |
| 2007/0118115 A1 | 5/2007 | Artale et al. |
| 2007/0123748 A1 | 5/2007 | Meglan |
| 2007/0130771 A1 | 6/2007 | Ehlert et al. |
| 2007/0135686 A1 | 6/2007 | Pruitt et al. |
| 2007/0149881 A1 | 6/2007 | Rabin |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0182842 A1 | 8/2007 | Sonnenschein et al. |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0270651 A1 | 11/2007 | Gilad et al. |
| 2007/0275348 A1 | 11/2007 | Lemon |
| 2007/0276424 A1 | 11/2007 | Mikkaichi et al. |
| 2007/0287933 A1 | 12/2007 | Phan et al. |
| 2008/0015413 A1 | 1/2008 | Barlow et al. |
| 2008/0015575 A1 | 1/2008 | Odom et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0082039 A1 | 4/2008 | Babaev |
| 2008/0082098 A1 | 4/2008 | Tanaka et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0281200 A1 | 11/2008 | Voic et al. |
| 2008/0281315 A1 | 11/2008 | Gines |

(56) References Cited

U.S. PATENT DOCUMENTS

| | | |
|---|---|---|
| 2008/0287948 A1 | 11/2008 | Newton et al. |
| 2008/0300588 A1 | 12/2008 | Groth et al. |
| 2008/0312502 A1 | 12/2008 | Swain et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0143678 A1 | 6/2009 | Keast et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0248021 A1 | 10/2009 | McKenna |
| 2009/0254080 A1 | 10/2009 | Honda |
| 2009/0270771 A1 | 10/2009 | Takahashi |
| 2009/0270853 A1 | 10/2009 | Yachi et al. |
| 2009/0287205 A1 | 11/2009 | Ingle |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0158307 A1 | 6/2010 | Kubota et al. |
| 2010/0187283 A1 | 7/2010 | Crainich et al. |
| 2010/0204802 A1 | 8/2010 | Wilson et al. |
| 2010/0222752 A1 | 9/2010 | Collins, Jr. et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2011/0009857 A1 | 1/2011 | Subramaniam et al. |
| 2011/0028964 A1 | 2/2011 | Edwards |
| 2011/0060333 A1* | 3/2011 | Mueller ............... A61B 17/295 606/46 |
| 2011/0087220 A1 | 4/2011 | Felder et al. |
| 2011/0087224 A1 | 4/2011 | Cadeddu et al. |
| 2011/0257680 A1 | 10/2011 | Reschke et al. |
| 2011/0270245 A1 | 11/2011 | Horner et al. |
| 2011/0276049 A1 | 11/2011 | Gerhardt |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0078139 A1 | 3/2012 | Aldridge et al. |
| 2012/0078244 A1 | 3/2012 | Worrell et al. |
| 2012/0085358 A1 | 4/2012 | Cadeddu et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0190759 A1* | 7/2013 | Waaler ............... H01M 2/1066 606/52 |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0194864 A1 | 7/2014 | Martin et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0263538 A1* | 9/2014 | Leimbach ........ A61B 17/07207 227/175.1 |
| 2014/0263541 A1 | 9/2014 | Leimbach et al. |
| 2014/0263552 A1 | 9/2014 | Hall et al. |
| 2014/0330271 A1 | 11/2014 | Dietz et al. |
| 2015/0032150 A1 | 1/2015 | Ishida et al. |
| 2015/0080876 A1 | 3/2015 | Worrell et al. |
| 2015/0209103 A1 | 7/2015 | Artale et al. |
| 2015/0230853 A1 | 8/2015 | Johnson et al. |
| 2015/0230861 A1 | 8/2015 | Woloszko et al. |
| 2015/0250531 A1 | 9/2015 | Dycus et al. |
| 2015/0272659 A1 | 10/2015 | Boudreaux et al. |
| 2015/0272660 A1 | 10/2015 | Boudreaux et al. |
| 2015/0305796 A1 | 10/2015 | Wang |
| 2015/0327918 A1 | 11/2015 | Sobajima et al. |
| 2016/0008023 A1 | 1/2016 | Yates et al. |
| 2016/0038225 A1 | 2/2016 | Couture et al. |
| 2016/0045248 A1 | 2/2016 | Unger et al. |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0066911 A1* | 3/2016 | Baber .................. G06F 1/266 307/52 |
| 2016/0066980 A1 | 3/2016 | Schall et al. |
| 2016/0074108 A1 | 3/2016 | Woodruff et al. |
| 2016/0128762 A1 | 5/2016 | Harris et al. |
| 2016/0143687 A1 | 5/2016 | Hart et al. |
| 2016/0157923 A1 | 6/2016 | Ding |
| 2016/0157927 A1 | 6/2016 | Corbett et al. |
| 2016/0175024 A1 | 6/2016 | Yates et al. |
| 2016/0175029 A1 | 6/2016 | Witt et al. |
| 2016/0175032 A1 | 6/2016 | Yang |
| 2016/0199123 A1 | 7/2016 | Thomas et al. |
| 2016/0199124 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2017/0056097 A1 | 3/2017 | Monson et al. |
| 2017/0105787 A1 | 4/2017 | Witt et al. |
| 2017/0105789 A1 | 4/2017 | Boudreaux et al. |
| 2017/0135751 A1 | 5/2017 | Rothweiler et al. |
| 2017/0164972 A1 | 6/2017 | Johnson et al. |
| 2017/0312014 A1 | 11/2017 | Strobl et al. |
| 2017/0312015 A1 | 11/2017 | Worrell et al. |
| 2017/0312016 A1 | 11/2017 | Strobl et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0325878 A1 | 11/2017 | Messerly et al. |
| 2017/0367751 A1 | 12/2017 | Ruddenklau et al. |
| 2018/0085156 A1 | 3/2018 | Witt et al. |
| 2018/0125571 A1 | 5/2018 | Witt et al. |
| 2018/0228530 A1 | 8/2018 | Yates et al. |
| 2018/0263683 A1 | 9/2018 | Renner et al. |
| 2018/0280075 A1 | 10/2018 | Nott et al. |
| 2018/0368906 A1 | 12/2018 | Yates et al. |
| 2019/0000468 A1 | 1/2019 | Adams et al. |
| 2019/0000470 A1 | 1/2019 | Yates et al. |
| 2019/0000528 A1 | 1/2019 | Yates et al. |
| 2019/0000530 A1 | 1/2019 | Yates et al. |
| 2019/0000555 A1 | 1/2019 | Schings et al. |
| 2019/0099209 A1 | 4/2019 | Witt et al. |
| 2019/0099212 A1 | 4/2019 | Davison et al. |
| 2019/0099213 A1 | 4/2019 | Witt et al. |
| 2019/0099217 A1 | 4/2019 | Witt et al. |

FOREIGN PATENT DOCUMENTS

| | | | |
|---|---|---|---|
| CN | 1694649 | A | 11/2005 |
| CN | 1922563 | A | 2/2007 |
| CN | 2868227 | Y | 2/2007 |

(56) References Cited

FOREIGN PATENT DOCUMENTS

| | | |
|---|---|---|
| CN | 102834069 A | 12/2012 |
| DE | 4300307 A1 | 7/1994 |
| DE | 19608716 C1 | 4/1997 |
| DE | 29623113 U1 | 10/1997 |
| DE | 20004812 U1 | 9/2000 |
| DE | 10201569 A1 | 7/2003 |
| DE | 102005032371 A1 | 1/2007 |
| EP | 0171967 A2 | 2/1986 |
| EP | 0443256 A1 | 8/1991 |
| EP | 0456470 A1 | 11/1991 |
| EP | 0340803 B1 | 8/1993 |
| EP | 0630612 A1 | 12/1994 |
| EP | 0482195 B1 | 1/1996 |
| EP | 0705571 A1 | 4/1996 |
| EP | 0612570 B1 | 6/1997 |
| EP | 0557806 B1 | 5/1998 |
| EP | 0640317 B1 | 9/1999 |
| EP | 0908148 B1 | 1/2002 |
| EP | 0722696 B1 | 12/2002 |
| EP | 1199044 B1 | 12/2005 |
| EP | 1293172 B1 | 4/2006 |
| EP | 0875209 B1 | 5/2006 |
| EP | 1704824 A1 | 9/2006 |
| EP | 1738795 A1 | 1/2007 |
| EP | 1749479 A1 | 2/2007 |
| EP | 1767157 A1 | 3/2007 |
| EP | 1254637 B1 | 8/2007 |
| EP | 1813201 A1 | 8/2007 |
| EP | 1844720 A1 | 10/2007 |
| EP | 1862133 A1 | 12/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1974771 A1 | 10/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1832259 B1 | 6/2009 |
| EP | 2074959 A1 | 7/2009 |
| EP | 1810625 B1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 2090239 B1 | 7/2011 |
| EP | 1728475 B1 | 8/2011 |
| EP | 2353518 A1 | 8/2011 |
| EP | 2436327 A1 | 4/2012 |
| EP | 2529681 A1 | 12/2012 |
| EP | 1767164 B1 | 1/2013 |
| EP | 2316359 B1 | 3/2013 |
| EP | 2090238 B1 | 4/2013 |
| EP | 2578172 A2 | 4/2013 |
| EP | 2508143 B1 | 2/2014 |
| ES | 2419159 A2 | 8/2013 |
| GB | 2032221 A | 4/1980 |
| GB | 2472216 A | 2/2011 |
| GB | 2447767 B | 8/2011 |
| JP | S537994 A | 1/1978 |
| JP | H08229050 A | 9/1996 |
| JP | 2002186627 A | 7/2002 |
| JP | 2008018226 A | 1/2008 |
| JP | 2009213878 A | 9/2009 |
| JP | 2010057926 A | 3/2010 |
| JP | 5714508 B2 | 5/2015 |
| WO | WO-8103272 A1 | 11/1981 |
| WO | WO-9222259 A2 | 12/1992 |
| WO | WO-9307817 A1 | 4/1993 |
| WO | WO-9314708 A1 | 8/1993 |
| WO | WO-9322973 A1 | 11/1993 |
| WO | WO-9510978 A1 | 4/1995 |
| WO | WO-9635382 A1 | 11/1996 |
| WO | WO-9710764 A1 | 3/1997 |
| WO | WO-9800069 A1 | 1/1998 |
| WO | WO-9837815 A1 | 9/1998 |
| WO | WO-9840020 A1 | 9/1998 |
| WO | WO-9857588 A1 | 12/1998 |
| WO | WO-9923960 A1 | 5/1999 |
| WO | WO-9940857 A1 | 8/1999 |
| WO | WO-9940861 A1 | 8/1999 |
| WO | WO-9947058 A2 | 9/1999 |
| WO | WO-0024330 A1 | 5/2000 |
| WO | WO-0024331 A1 | 5/2000 |
| WO | WO-0025691 A1 | 5/2000 |
| WO | WO-0128444 A1 | 4/2001 |
| WO | WO-0154590 A1 | 8/2001 |
| WO | WO-0195817 A1 | 12/2001 |
| WO | WO-02062241 A1 | 8/2002 |
| WO | WO-02080794 A1 | 10/2002 |
| WO | WO-02080797 A1 | 10/2002 |
| WO | WO-03001986 A2 | 1/2003 |
| WO | WO-03013374 A1 | 2/2003 |
| WO | WO-03020339 A2 | 3/2003 |
| WO | WO-03028541 A2 | 4/2003 |
| WO | WO-03030708 A2 | 4/2003 |
| WO | WO-03068046 A2 | 8/2003 |
| WO | WO-2004011037 A2 | 2/2004 |
| WO | WO-2004032754 A2 | 4/2004 |
| WO | WO-2004032762 A1 | 4/2004 |
| WO | WO-2004032763 A2 | 4/2004 |
| WO | WO-2004078051 A2 | 9/2004 |
| WO | WO-2004084709 A2 | 10/2004 |
| WO | WO-2004112618 A2 | 12/2004 |
| WO | WO-2005002415 A2 | 1/2005 |
| WO | WO-2005009211 A2 | 2/2005 |
| WO | WO-2005052959 A2 | 6/2005 |
| WO | WO-2005122917 A1 | 12/2005 |
| WO | WO-2006021269 A1 | 3/2006 |
| WO | WO-2006036706 A1 | 4/2006 |
| WO | WO-2006042210 A2 | 4/2006 |
| WO | WO-2006055166 A2 | 5/2006 |
| WO | WO-2006119139 A2 | 11/2006 |
| WO | WO-2006129465 A1 | 12/2006 |
| WO | WO-2007047531 A2 | 4/2007 |
| WO | WO-2007063550 A2 | 6/2007 |
| WO | WO-2007130382 A2 | 11/2007 |
| WO | WO-2007143665 A2 | 12/2007 |
| WO | WO-2008020964 A2 | 2/2008 |
| WO | WO-2008031025 A2 | 3/2008 |
| WO | WO-2008035089 A1 | 3/2008 |
| WO | WO-2008045348 A2 | 4/2008 |
| WO | WO-2008099529 A1 | 8/2008 |
| WO | WO-2008101356 A1 | 8/2008 |
| WO | WO-2008130793 A1 | 10/2008 |
| WO | WO-2009018406 A2 | 2/2009 |
| WO | WO-2009022614 A1 | 2/2009 |
| WO | WO-2009027065 A1 | 3/2009 |
| WO | WO-2009036818 A1 | 3/2009 |
| WO | WO-2009039179 A1 | 3/2009 |
| WO | WO-2009059741 A1 | 5/2009 |
| WO | WO-2009067649 A2 | 5/2009 |
| WO | WO-2009082477 A2 | 7/2009 |
| WO | WO-2009149234 A1 | 12/2009 |
| WO | WO-2010017266 A2 | 2/2010 |
| WO | WO-2010056716 A2 | 5/2010 |
| WO | WO-2010083480 A2 | 7/2010 |
| WO | WO-2010104755 A1 | 9/2010 |
| WO | WO-2011008672 A2 | 1/2011 |
| WO | WO-2011044343 A2 | 4/2011 |
| WO | WO-2011044468 A2 | 4/2011 |
| WO | WO-2011044471 A2 | 4/2011 |
| WO | WO-2011084768 A1 | 7/2011 |
| WO | WO-2011089717 A1 | 7/2011 |
| WO | WO-2011144911 A1 | 11/2011 |
| WO | WO-2011146691 A2 | 11/2011 |
| WO | WO-2011146698 A2 | 11/2011 |

(56) References Cited

FOREIGN PATENT DOCUMENTS

| WO | WO-2011146709 A2 | 11/2011 |
|---|---|---|
| WO | WO-2012044606 A2 | 4/2012 |
| WO | WO-2012061638 A1 | 5/2012 |
| WO | WO-2012166510 A1 | 12/2012 |
| WO | WO-2013034629 A1 | 3/2013 |
| WO | WO-2013062978 A2 | 5/2013 |
| WO | WO-2013102602 A2 | 7/2013 |
| WO | WO-2013131823 A1 | 9/2013 |
| WO | WO-2013154157 A1 | 10/2013 |
| WO | WO-2015017989 A1 | 2/2015 |
| WO | WO-2015017995 A1 | 2/2015 |
| WO | WO-2015197395 A8 | 12/2015 |

OTHER PUBLICATIONS

Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

Park et al., "Trocar-less Instrumentation for Laparoscopy: Magnetic Positioning of Intra-Abdominal Camera and Retractor", Annals of Surgery, vol. 245, No. 3, pp. 379-384, Mar. 2007.

Hörmann et al., "Reversible and irreversible denaturation of collagen fibers." Biochemistry, 10, pp. 932-937 (1971).

Scott et al., "Trans gastric, transcolonic, and transvaginal cholecystectomy using magnetically anchored instruments," SAGES Annual Meeting Poster, 2007.

Scott et al., "Optimizing magnetically anchored camera, light source, graspers, and cautery dissector for transvaginal notes cholecystectomy," Submitted for Presentation, SAGES Annual Meeting, 2008.

Duchene et al., "Magnetic positioning system for trocarless laparoscopic instruments," Engineering and Urology Society Poster, 2004.

Scott et al., "Transvaginal single access 'pure' NOTES sleeve gastrectomy using a deployable magnetically anchored video camera," Digestive Disease Week (DDW), American Society for Gastrointestinal Endoscopy (ASGE) Annual Meeting Poster, 2008.

Leonard I. Malis, M.D., "The Value of Irrigation During Bipolar Coagulation," 1989.

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

Technology Overview, printed from www.harmonicscalpel.com, Internet site, website accessed on Jun. 13, 2007, (3 pages).

Scott et al., "Short-term survival outcomes following transvaginal NOTES cholecystectomy using magnetically anchored instruments," Oral Presentation, ASGE Annual Meeting/DDW, 2007.

Cadeddu et al., "Magnetic positioning system for trocarless laparoscopic instruments," American College of Surgeons Poster, 2004.

Scott et al., "Evaluation of a novel air seal access port for transvaginal notes cholecystectomy," Submitted for Presentation, SAGES Annual Meeting, 2008.

Scott et al., "Magnetically anchored instruments for transgastric endoscopic surgery," Oral Presentation for SAGES Annual Meeting, Emerging Technology Oral Abstract ET005, 2006.

Scott et al., "Transvaginal NOTES cholecystectomy using magnetically anchored instruments," Abstract for Video Submission, ASGE IIIh Annual Video Forum, 2007.

Scott et al., "A randomized comparison of laparoscopic, flexible endoscopic, and wired and wireless magnetic NOTES cameras on ex-vivo and in-vivo surgical performance," Digestive Disease Week (DDW), American Society for Gastrointestinal Endoscopy (ASGE) Annual Meeting Abstract, 2008.

Rapaccini et al., "Gastric Wall Thickness in Normal and Neoplastic Subjects: A Prospective Study Performed by Abdominal Ultrasound", Gastrointestinal Radiology, vol. 13, pp. 197-199. 1988.

Gedeon et al., "Maximizing coupling strength of magnetically anchored notes instruments: How thick can we go?" SAGES Annual Meeting Poster, 2008.

Gedeon et al., "Maximizing coupling strength of magnetically anchored notes instruments: How thick can we go?" Submittedfor Presentation, Poster, SAGES Annual Meeting, 2008.

Fernandez et al., "Development of a transabdominal anchoring system for trocar-less laparoscopic surgery," ASME Proceedings of/MECE, 2003.

Cadeddu et al., "Transabdominal magnetic anchoring system for trocar-less laparoscopic surgery," American Urological Association Poster, 2002.

Cadeddu et al., "Transabdominal magnetic anchoring system for trocar-less laparoscopic surgery," Journal of Urology Abstract, 2002.

Castellvi et al., "Completely transvaginal NOTES cholecystectomy in a porcine model using novel endoscopic instrumentation," Accepted for Poster Presentation, SAGES Annual Meeting, 2009.

Castellvi et al., "Hybrid transvaginal NOTES sleeve gastrectomy in a porcine model using a magnetically anchored camera and novel instrumentation," Accepted for Poster Presentation, SAGES Annual Meeting, 2009.

Scott et al., "Completely transvaginal NOTES cholecystectomy using magnetically anchored instruments," Surg. Endosc., 21:2308-2316, 2007.

Raman et al., "Complete transvaginal NOTES nephrectomy using magnetically anchored instrumentation," Journal of Endourology, 23(3):, 2009.367-371,2009.

Peirs et al., "A miniature manipulator for integration in self-propelling endoscope," Sensors and Actuators, 92:343-9, 2001.

Cadeddu et al., "Novel magnetically guided intra-abdominal camera to facilitate laparoendoscopic single site surgery: initial human experience," Surgical Endoscopy, SAGES Oral Manuscript, 2009.

Castellvi et al., "Hybrid transgastric NOTES cholecystectomy in a porcine model using a magnetically anchored cautery and novel instrumentation," Submitted for Presentation, ASGE, 2009.

Swain et al., "Linear stapler formation of ileo-rectal, entero-enteral and gastrojejunal anastomoses during dual and single access 'pure' NOTES procedures: Methods, magnets and stapler modifications," Digestive Disease Week (DDW), American Society for Gastrointestinal Endoscopy (ASGE) Annual Meeting Abstract, 2008.

Swain et al., "Wireless endosurgery for NOTES," Digestive Disease Week (DDVV), American Society for Gastrointestinal Endoscopy (ASGE) Annual Meeting Abstract, 2008.

Tang et al., "Live video manipulator for endoscopy and natural orifice transluminal endoscopic surgery (with videos)," Gastrointestinal Endoscopy, 68:559-564, 2008.

Zeltser et al., "Single trocar laparoscopic nephrectomy using magnetic anchoring and guidance system in the porcine model," The Journal of Urology, 178:288-291, 2007.

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Abbott, et al. Proceedings of the 2007 IEEEIRDJ International Conference on Intelligent Robots and Systems. 410-416, 2007.

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

(56) References Cited

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Chen et al., "Heat-induced changes in the mechanics of a collagenous tissue: pseudoelastic behavior at 37° C.," Journal of Biomechanics, 31, pp. 211-216 (1998).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Campbell et al, "Thermal Imaging in Surgery," p. 19-3, in Medical Infrared Imaging, N. A. Diakides and J. D. Bronzino, Eds. (2008).
F. A. Duck, "Optical Properties of Tissue Including Ultraviolet and Infrared Radiation," pp. 43-71 in Physical Properties of Tissue (1990).
Lim et al., "A Review of Mechanism Used in Laparoscopic Surgical Instruments," Mechanism and Machine Theory, vol. 38, pp. 1133-1147, (2003).
AST Products, Inc., "Principles of Video Contact Angle Analysis," 20 pages, (2006).
Wall et al., "Thermal modification of collagen," J Shoulder Elbow Surg, No. 8, pp. 339-344 (Jul./Aug. 1999).
Covidien Brochure, [Value Analysis Brief], LigaSure Advance™ Pistol Grip, dated Rev. Apr. 2010 (7 pages).
Kurt Gieck & Reiner Gieck, *Engineering Formulas* § Z.7 (7th ed. 1997).
Covidien Brochure, The LigaSure Precise™ Instrument, dated Mar. 2011 (2 pages).
Covidien Brochure, The LigaSure™ 5 mm Blunt Tip Sealer/Divider Family, dated Apr. 2013 (2 pages).
National Semiconductors Temperature Sensor Handbook—http://www.national.com/appinfo/tempsensors/files/temphb.pdf; accessed online: Apr. 1, 2011.
Sullivan, "Optimal Choice for Number of Strands in a Litz-Wire Transformer Winding," IEEE Transactions on Power Electronics, vol. 14, No. 2, Mar. 1999, pp. 283-291.
Douglas, S.C. "Introduction to Adaptive Filter". Digital Signal Processing Handbook. Ed. Vijay K. Madisetti and Douglas B. Williams. Boca Raton: CRC Press LLC, 1999.
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Covidien Brochure, LigaSure Atlas™ Hand Switching Instruments, dated Dec. 2008 (2 pages).
Covidien Brochure, LigaSure Impact™ Instrument LF4318, dated Feb. 2013 (3 pages).
Wright, et al., "Time-Temperature Equivalence of Heat-Induced Changes in Cells and Proteins," Feb. 1998. ASME Journal of Biomechanical Engineering, vol. 120, pp. 22-26.
Humphrey, J.D., "Continuum Thermomechanics and the Clinical Treatment of Disease and Injury," Appl. Mech. Rev., vol. 56, No. 2 pp. 231-260 (Mar. 2003).
Gibson, "Magnetic Refrigerator Successfully Tested," U.S. Department of Energy Research News, accessed online on Aug. 6, 2010 at http://www.eurekalet.org/features/doe/2001-11/dl-mrs062802.php (Nov. 1, 2001).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Moran et al., "Thermally Induced Shrinkage of Joint Capsule," Clinical Orthopaedics and Related Research, No. 281, pp. 248-255 (Dec. 2000).
Lee et al., "A multi-sample denaturation temperature tester for collagenous biomaterials," Med. Eng. Phy., vol. 17, No. 2, pp. 115-121 (Mar. 1995).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Chen et al., "Heat-Induced Changes in the Mechanics of a Collagenous Tissue: Isothermal Free Shrinkage," Transactions of the ASME, vol. 119, pp. 372-378 (Nov. 1997).
Glaser and Subak-Sharpe, Integrated Circuit Engineering, Addison-Wesley Publishing, Reading, MA (1979). (book—not attached).

\* cited by examiner

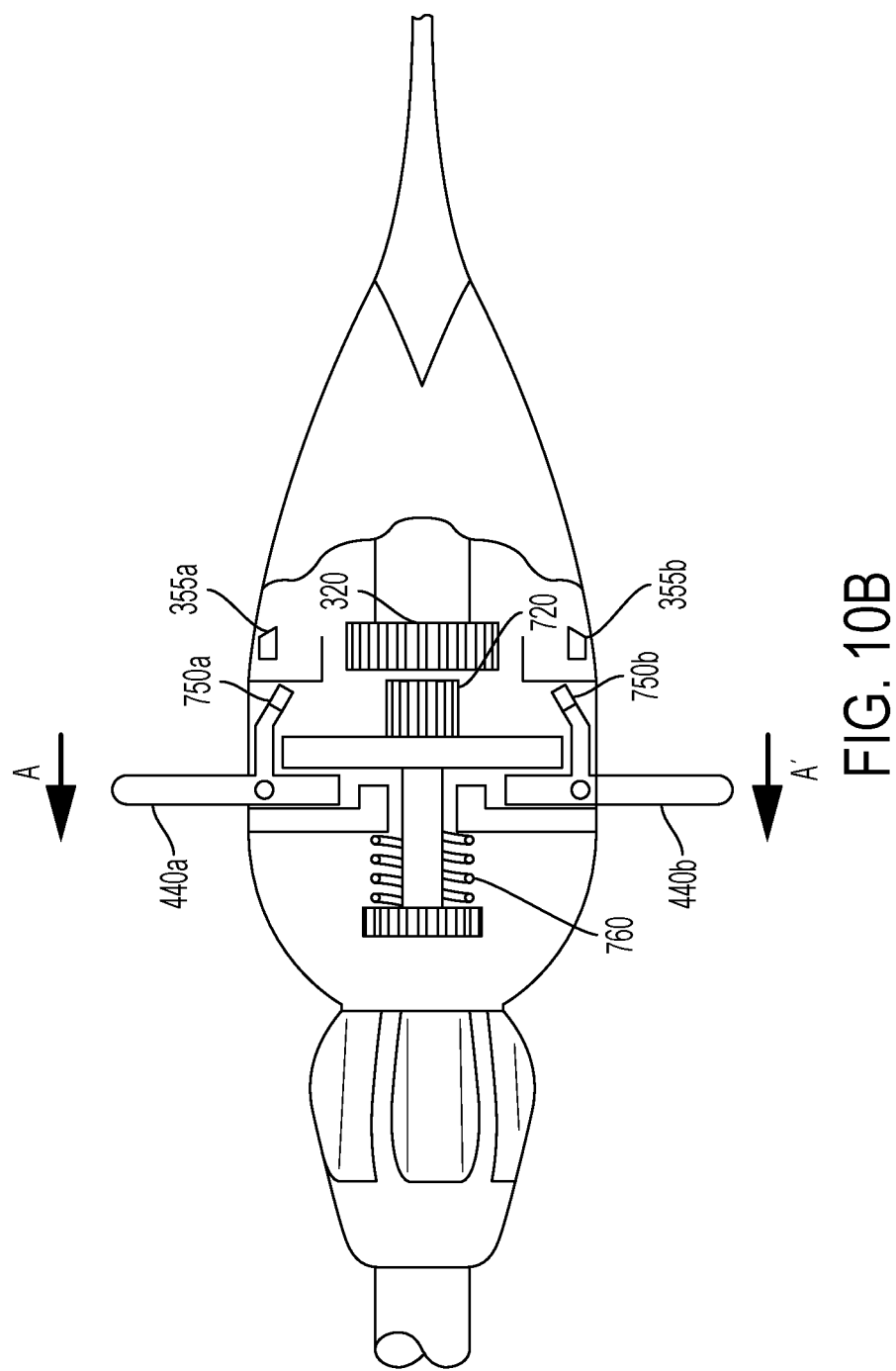

ENERGIZED MEDICAL DEVICE WITH REUSABLE HANDLE

BACKGROUND

Electrosurgical devices are used in many surgical operations. Electrosurgical devices apply electrical energy to tissue in order to treat tissue. An electrosurgical device may comprise an instrument having a distally-mounted end effector comprising one or more electrodes. The end effector can be positioned against tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active (or source) electrode of the end effector and returned through a return electrode (e.g., a grounding pad) separately located on a patient's body. Heat generated by the current flow through the tissue may form hemostatic seals within the tissue and/or between tissues and thus may be particularly useful for sealing blood vessels, for example. The end effector of an electrosurgical device sometimes also comprises a cutting member that is movable relative to the tissue and the electrodes to transect the tissue.

Electrical energy applied by an electrosurgical device can be transmitted to the instrument by a generator. The electrical energy may be in the form of radio frequency ("RF") energy that may be in a frequency range described in EN 60601-2-2:2009+A11:2011, Definition 201.3.218—HIGH FREQUENCY. For example, the frequency in monopolar RF applications are typically restricted to less than 5 MHz. However, in bipolar RF applications, the frequency can be almost anything. Frequencies above 200 kHz can be typically used for MONOPOLAR applications in order to avoid the unwanted stimulation of nerves and muscles which would result from the use of low frequency current. Lower frequencies may be used for BIPOLAR techniques if the RISK ANALYSIS shows the possibility of neuromuscular stimulation has been mitigated to an acceptable level. Normally, frequencies above 5 MHz are not used in order to minimize the problems associated with HIGH FREQUENCY LEAKAGE CURRENTS. However, higher frequencies may be used in the case of BIPOLAR techniques. It is generally recognized that 10 mA is the lower threshold of thermal effects on tissue. During its operation, an electrosurgical device can transmit RF energy through tissue, which can cause ionic agitation, or friction, in effect resistive heating or Joule heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

Electrosurgical devices may incorporate additional features in addition to the end effector and electrodes. In some non-limiting examples, such electrosurgical devices may include mechanisms to clamp tissue together, such as a stapling device, and/or mechanisms to sever tissue, such as a tissue knife. An electrosurgical device may include a shaft for placing the end effector proximate to tissue undergoing treatment. The shaft may be straight or curved, bendable or non-bendable. In an example of an electrosurgical device including a straight and bendable shaft, the shaft may include one or more articulation joints to permit controlled bending of the shaft. Such joints may permit a user of the electrosurgical device to place the end effector in contact with tissue at an angle to the shaft when the tissue being treated is not readily accessible using an electrosurgical device having a straight, non-bending shaft.

SUMMARY

In one aspect, an electrosurgical device may include a reusable handle. The reusable handle may include a housing, a motor disposed within the housing, a controller configured to actuate the motor, an electrical interface portion configured to interface with a front portion of the electrosurgical device, and a mechanical interface portion configured to interface with the front portion of the electrosurgical device. The electrical interface portion may include a plurality of sensors including at least a knife actuation sensor, a cauterization actuation sensor, and an articulation actuation sensor, as well as and at least one tissue cauterization current terminal. Each of the plurality of sensors may be in data communication with the controller. The mechanical interface portion may include a first mechanical coupling configured to couple one or more motions of the motor to a tissue cutting mechanism, a second mechanical coupling configured to couple the one or more motions of the motor to an articulation mechanism, and a latching mechanism configured to releasably latch the front portion of the electrosurgical device to the housing.

In one aspect of a reusable handle, the plurality of sensors incorporates one or more of a Hall sensor, an RF sensor, an optical sensor, and an electronic sensor.

In one aspect of a reusable handle, the first mechanical coupling and the second mechanical coupling independently comprise one or more of a spur gear, a worm gear, a planetary gear set, a helical gear, a bevel gear, a miter gear, and a rack and pinion gear set.

In one aspect of a reusable handle, the reusable handle further incorporates one or more power sources configured to supply power to the motor and the controller.

In one aspect of a reusable handle, the one or more power sources incorporate one or more batteries disposed within the housing.

In one aspect of a reusable handle, the reusable handle further incorporates a source of tissue cauterization power in electrical communication with the at least one tissue cauterization power terminal.

In one aspect of a reusable handle, the source of tissue cauterization power incorporates one or more batteries disposed within the housing.

In one aspect of a reusable handle, the controller is configured to activate the one or more motions of the motor at least in response to receiving data from one or more of the a plurality of sensors.

In one aspect of a reusable handle, the reusable handle further incorporates an identification sensor configured to receive identification information from the front portion of the electrosurgical device.

In one aspect of a reusable handle, the second mechanical coupling is configured to couple the one or more motions of the motor to the articulation mechanism independent of a coupling of the one or more motions of the motor to the tissue cutting mechanism.

In one aspect, an electrosurgical system may include a front portion assembly, a reusable handle assembly, and a latching mechanism in which the front portion assembly is releasably attached to the reusable handle assembly. The front portion assembly may include a front portion housing, an end effector comprising a first jaw movably disposed to contact a second jaw, a first electrode configured to be in electrical communication with a first RF current terminal, and a second electrode configured to be in electrical communication with a second RF current terminal, a tissue knife movably disposed within the end effector, a tissue knife advancement component configured to move the tissue knife within the end effector, a jaw closure trigger, a knife advancement control, an energy activation control, and an elongated shaft having a distal end in mechanical communication with the end effector. The reusable handle assembly may include a reusable handle housing, a motor disposed within the reusable handle housing, a controller configured to actuate the motor, an electrical interface portion configured to interface with the front portion assembly, a mechanical interface portion configured to interface with the front portion of the electrosurgical device, and a latching mechanism configured to releasably latch the front portion housing to the reusable handle housing. The electrical interface portion may include a knife actuation sensor configured to sense a position of the knife advancement control, a cauterization actuation sensor configured to sense a position of the energy activation control, an articulation actuation sensor, the first RF current terminal, and the second RF current terminal. The knife actuation sensor, the cauterization actuation sensor, and the articulation actuation sensor may be in data communication with the controller. The mechanical interface portion may include a first mechanical coupling configured to couple one or more motions of the motor to the tissue knife advancement component, and a second mechanical coupling configured to couple the one or more motions of the motor to an articulation mechanism. In one example of the electrosurgical system, the front portion assembly may further include an articulation joint in the elongated shaft, in which the articulation joint is configured to permit the shaft to move in a plane orthogonal to a plane of a motion of the first jaw with respect to the second jaw, an articulation mechanism configured to move the articulation joint, and an articulation control in which the articulation actuation sensor is configured to sense the position of the articulation control.

In one aspect of an electrosurgical system, the front portion assembly further incorporates: an articulation joint in the elongated shaft, in which the articulation joint is configured to permit the shaft to move in a plane orthogonal to a plane of a motion of the first jaw with respect to the second jaw; an articulation mechanism, configured to move the articulation joint; and an articulation control, in which the articulation actuation sensor is configured to sense the position of the articulation control.

In one aspect of an electrosurgical system, the knife actuation sensor, the cauterization actuation sensor, and the articulation actuation sensor independently comprise one or more of a Hall sensor, an RF sensor, an optical sensor, and an electronic sensor.

In one aspect of an electrosurgical system, the front portion assembly releasably attached to the reusable handle assembly incorporates an electrosurgical system configured for single-handed operation.

In one aspect of an electrosurgical system, the electrosurgical system further incorporates an RF current source in electrical communication with the first RF current terminal and the second RF current terminal.

In one aspect of an electrosurgical system, the electrosurgical system further incorporates: an information storage device disposed within the front portion assembly; and an identification sensor disposed within the reusable handle assembly, in which the identification sensor is in data communication with the controller, and in which the identification sensor is configured to receive information from the information storage device.

In one aspect of an electrosurgical system, the information storage device comprises one or more of a non-volatile device, a read/write device, and a WORM device.

In one aspect of an electrosurgical system, the information storage device comprises one or more of an RFID tag, a PROM device, an EPROM device, and an EEPROM device.

In one aspect of an electrosurgical system, the information comprises one or more of an identifier of a front portion assembly type, a front portion assembly model number, a front portion assembly serial number, a value of the number of uses of the front portion assembly, and a configuration of one or more components of the front portion assembly.

In one aspect, a method of using an electrosurgical system may include providing a front portion assembly having a front portion housing, providing a reusable handle assembly having a reusable handle housing, contacting the front portion assembly with the reusable handle assembly and releasably latching the front portion housing to the reusable handle housing. The front portion assembly may further include an end effector comprising a first jaw movably disposed to contact a second jaw, a first electrode configured to be in electrical communication with a first RF current terminal, and a second electrode configured to be in electrical communication with a second RF current terminal, a tissue knife movably disposed within the end effector, a tissue knife advancement component configured to move the tissue knife within the end effector, a jaw closure trigger, a knife advancement control, an energy activation control, and an elongated shaft having a distal end in mechanical communication with the end effector. The reusable handle assembly may further include a motor disposed within the reusable handle housing; a controller configured to actuate the motor; an electrical interface portion configured to interface with the front portion assembly, a mechanical interface portion configured to interface with the front portion assembly, and a latching mechanism configured to releasably latch the front portion housing to the reusable handle housing.

The electrical interface portion may include a knife actuation sensor configured to sense a position of the knife advancement control, a cauterization actuation sensor configured to sense a position of the energy activation control, an articulation actuation sensor, the first RF current terminal, and the second RF current terminal. The knife actuation sensor, the cauterization actuation sensor, and the articulation actuation sensor may be in data communication with the controller.

The mechanical interface portion may include a first mechanical coupling configured to couple one or more motions of the motor to the tissue knife advancement component and a second mechanical coupling configured to couple the one or more motions of the motor to an articulation mechanism.

The method may further include using the jaw closure trigger to move the first jaw relative to the second jaw thereby capturing a material therebetween, moving the energy activation control, sensing, by the cauterization activation sensor, the position of the energy activation control, causing an RF current to flow between the first RF current terminal and the second RF current terminal when the position of the energy activation control sensed by the cauterization activation sensor is at least at a predetermined position, sensing, by the knife actuation sensor, the position of the knife advancement control, and causing, by the controller, the motor to move the tissue knife advancement component via the first mechanical coupling when the position of the knife advancement control sensed by the knife actuation sensor is at least at a predetermined position. In one example of the method, the front portion assembly may further include an articulation joint in the elongated shaft, in which the articulation joint is configured to permit the shaft to move in a plane orthogonal to a plane of a motion of the first jaw with respect to the second jaw, an articulation mechanism configured to move the articulation joint, and an articulation control.

The example of the method may further include having the articulation actuation sensor configured to sense the position of the articulation control, sensing, by the articulation actuation sensor, the position of the articulation control, and causing, by the controller, the motor to move the articulation mechanism via the second mechanical coupling when the position of the articulation control sensed by the articulation actuation sensor is at least at a predetermined position.

In one aspect of the method of using an electrosurgical system, providing a front portion assembly further incorporates providing a front portion assembly comprising: an articulation joint in the elongated shaft, in which the articulation joint is configured to permit the shaft to move in a plane orthogonal to a plane of a motion of the first jaw with respect to the second jaw; the articulation mechanism, configured to move the articulation joint; and an articulation control; in which providing a reusable handle assembly further comprises providing a reusable handle assembly wherein the articulation actuation sensor is configured to sense the position of the articulation control; sensing, by the articulation actuation sensor, the position of the articulation control; and causing, by the controller, the motor to move the articulation mechanism via the second mechanical coupling when the position of the articulation control sensed by the articulation actuation sensor is at least at a predetermined position.

BRIEF DESCRIPTION OF THE FIGURES

The features of the various aspects are set forth with particularity in the appended claims. The various aspects, however, both as to organization and methods of operation, together with advantages thereof, may best be understood by reference to the following description, taken in conjunction with the accompanying drawings as follows:

FIG. 10 illustrates a perspective view of a portion of one aspect of an electrosurgical device, according to one aspect of the present disclosure.

FIG. 10B illustrates a top sectional view of a proximal end of the front portion housing of one aspect of the electrosurgical device illustrated in FIG. 4, according to one aspect of the present disclosure.

DETAILED DESCRIPTION

Figure 1A:
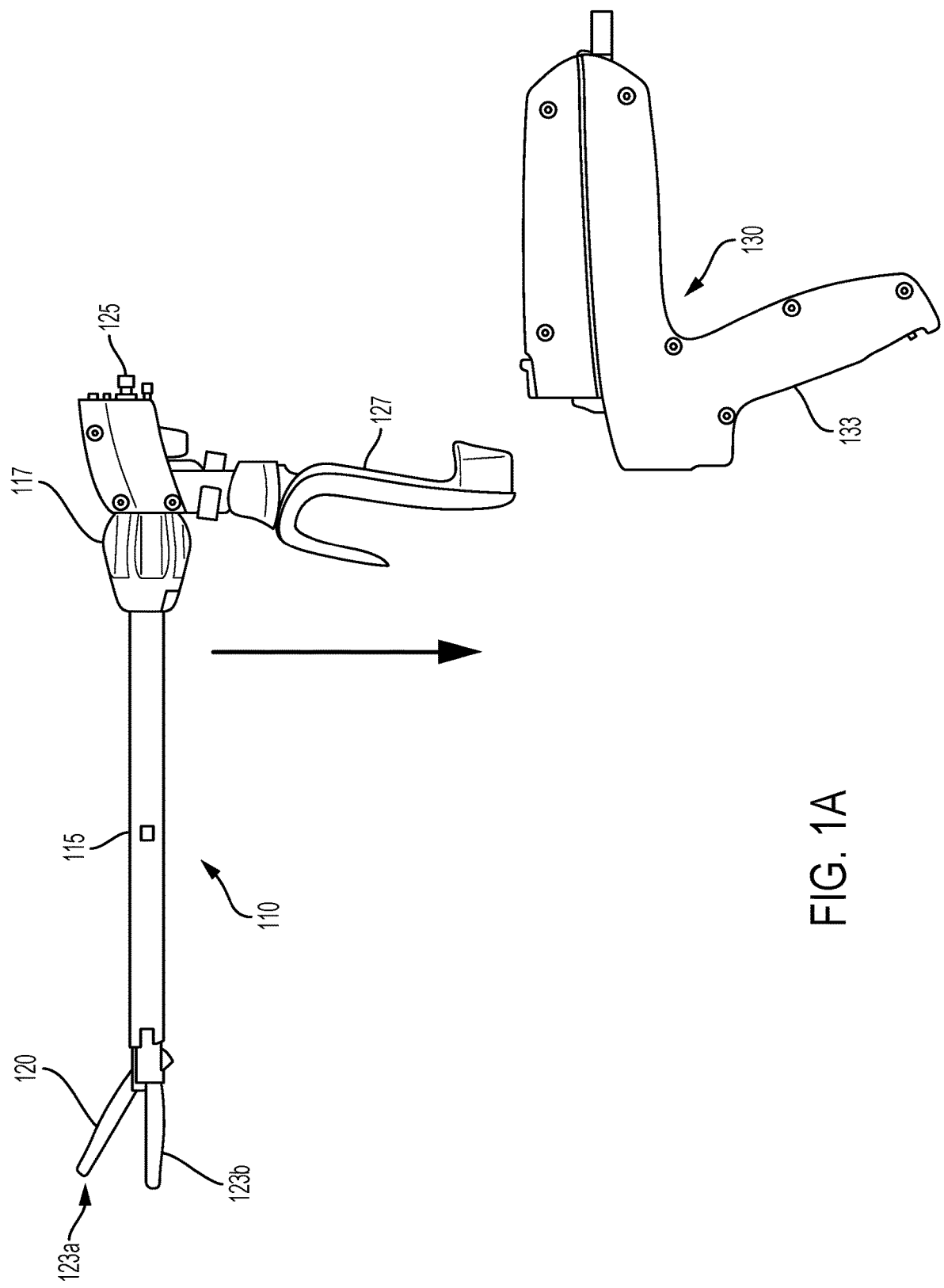
FIG. 1A illustrates a perspective view of one aspect of an electrosurgical device separated into a front portion assembly and a reusable handle assembly, according to one aspect of the present disclosure.

Reference will now be made in detail to several aspects, including example implementations of electrosurgical medical instruments for cutting and coagulating tissue. Wherever practicable similar or like reference numbers may be used in the figures and may indicate similar or like functionality. The figures depict examples of the disclosed surgical instruments and/or methods of use for purposes of illustration only. One skilled in the art will readily recognize from the following description that alternative examples of the structures and methods illustrated herein may be employed without departing from the principles described herein.

Various aspects of surgical instruments use therapeutic and/or sub-therapeutic electrical energy to treat tissue. One aspects are adapted for use in a hand operated manner, although electrosurgical instruments may be utilized in robotic applications as well. In one non-limiting example, an electrosurgical system may include a proximal handle, a distal working end or end effector, and an introducer or elongated shaft disposed in-between.

The electrosurgical system can be configured to source energy, such as electrical energy, RF energy, ultrasonic energy, heat energy, or any combination thereof, to the tissue of a patient either independently or simultaneously. In one example, the electrosurgical system may include a power source in electrical communication with the electrosurgical instrument. The power source may be connected to the electrosurgical instrument via a suitable transmission medium such as a cable. The power source may be separate from the electrosurgical instrument or may be formed integrally with the electrosurgical instrument to form a unitary electrosurgical system. In one non-limiting example, the power source may include one or more batteries located within a portion of the electrosurgical instrument. It may be understood that the power source may source energy for use on the tissue of the patient as well as for any other electrical use by the electrosurgical system, including, without limitation, lights, sensors, communication systems, indicators, and displays.

As disclosed above, an electrosurgical system may incorporate components to grasp a tissue via an end effector, deliver energy to the tissue via one or more electrodes, and cut the tissue via a dissecting device such as a tissue knife. The structural capabilities of any aspect of an electrosurgical system may be designed for use in one or more of a variety of surgical procedures. In some surgical procedures, the treated tissue may be readily accessible to an end effector affixed to a relatively straight and unbendable shaft. In some alternative surgical procedures, the tissue may not be readily accessible to the end effector on such a shaft. In such procedures, the electrosurgical system may incorporate a shaft designed to bend so that the end effector may contact the tissue requiring treatment. However, despite such differences between electrosurgical systems, many electrosurgical systems incorporate common features of use, such as tissue grasping, cauterizing, and cutting. Consequently, it may be recognized that a modular design for electrosurgical systems may be useful to reduce the number and types of devices required for such surgeries. Thus, a front portion assembly may be designed for a specific surgical procedure, while a reusable handle assembly, configured to releasably attach to a front portion assembly, may be designed to provide control of surgical functions common to each front portion assembly.

It may be recognized that the reusable handle assembly may also be designed to automate common functions of the electrosurgical device. Device intelligence may be provided by a controller located in the reusable handle assembly that is configured to receive information from a front portion assembly. Such information may include data regarding the type and use of the front portion assembly. Alternatively, information may include data indicative of the position and/or activation of control components (such as buttons or slides which can be manipulated) that may indicate what system functions should be activated and in what manner.

Figure 1B:
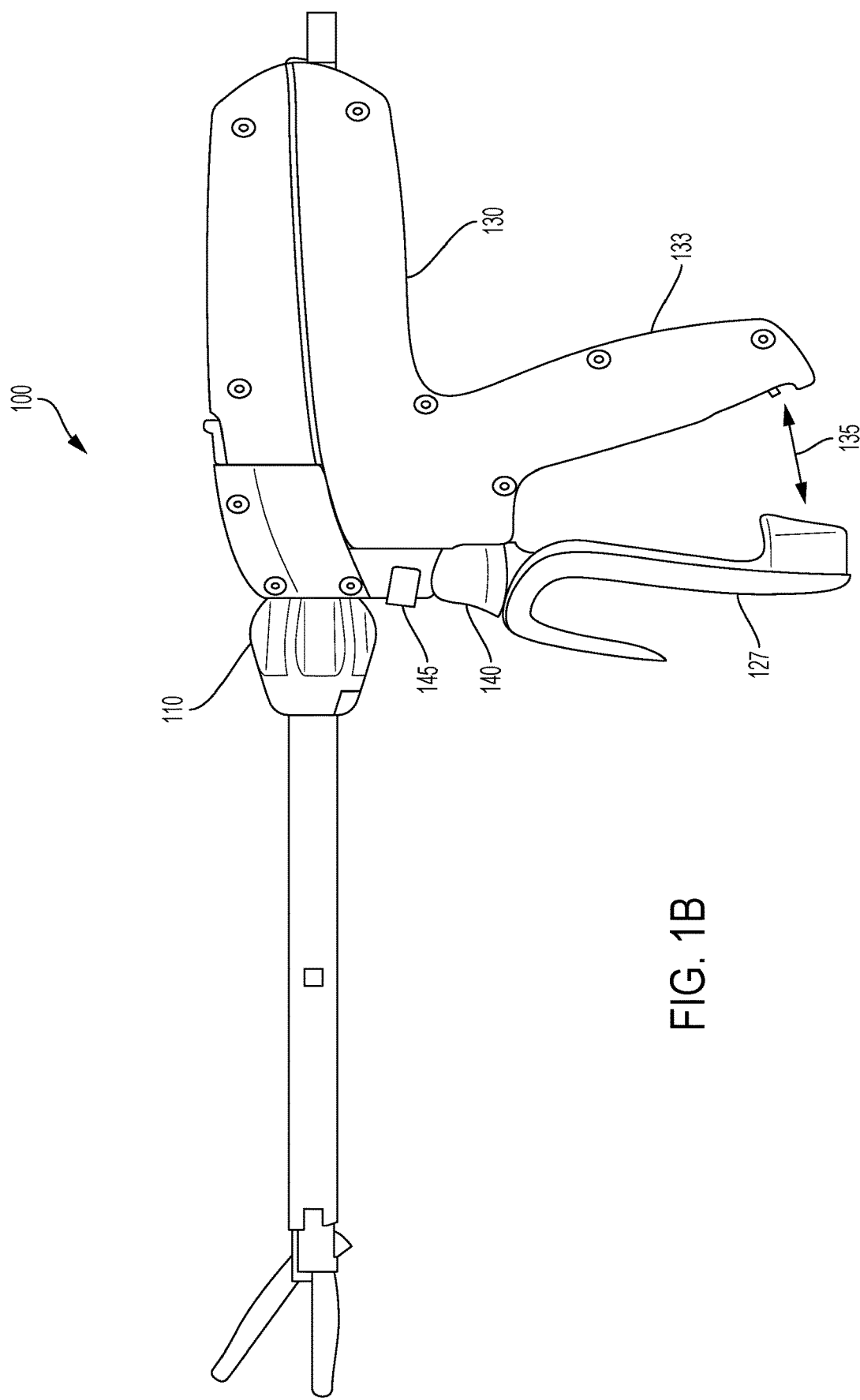
FIG. 1B illustrates a perspective view of one aspect of an electrosurgical device, according to one aspect of the present disclosure.
Figure 1C:
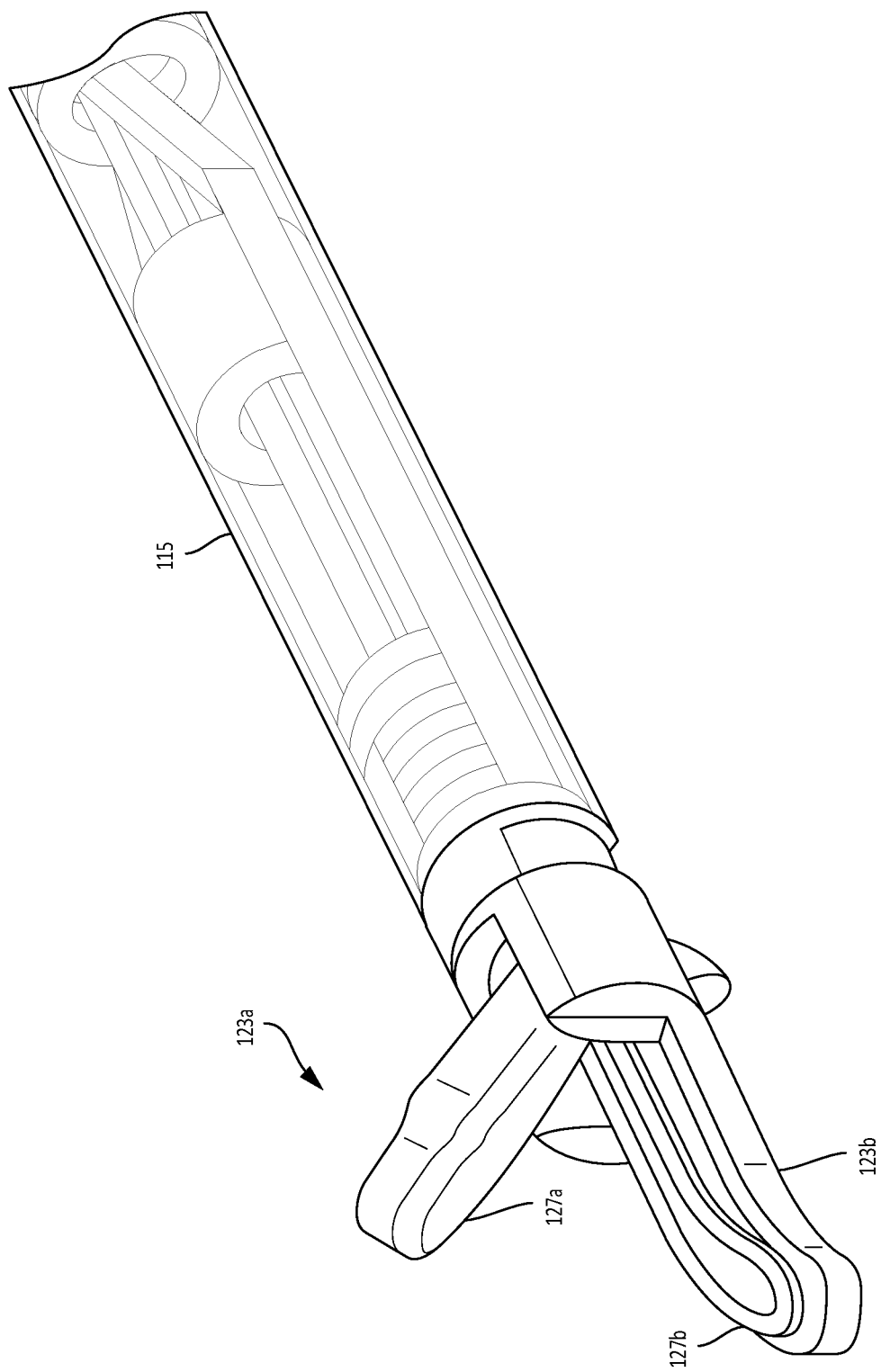

FIGS. 1A, 1B, and 1C are perspective views of one example of an electrosurgical instrument 100. FIG. 1A illustrates the electrosurgical instrument 100 disassembled into a front portion assembly 110 and a reusable handle assembly 130. The front portion assembly 110 may include a shaft 115 affixed to a front portion housing at a proximal end, and an end effector 120 at a distal end. The end effector 120 may include a pair of opposable jaws 123a, 123b. In a non-limiting example, the shaft 115 may be rotatable through the rotary motion of a shaft rotation knob 117. The shaft 115 may have a cylindrical or rectangular cross-section, for example, and can comprise a thin-wall tubular sleeve that extends from the front portion assembly housing. The shaft 115 may include a bore extending therethrough for carrying actuator mechanisms, for example, an axially moveable member for actuating the jaws 123a, 123b and for carrying electrical leads for delivery of electrical energy to electrosurgical components of the end effector 120. The front portion assembly may include a jaw closure trigger 127 configured to adjust the position of the jaws 123a, 123b with respect to each other. In one non-limiting example, the jaw closure trigger 127 may be coupled to an axially moveable member disposed within the shaft 115 by a shuttle operably engaged to an extension of the jaw closure trigger 127. The front portion assembly 110 may also include a proximal interface end 125 designed to contact an equivalent distal interface end of the reusable handle assembly 130. The reusable handle assembly 130 may include a reusable handle housing including a handle 133 that may operate in conjunction with the jaw closure trigger 127 to permit control of the motion of the jaws 123a, 123b. The front portion assembly 110 may be configured to carry actuator levers, triggers or sliders for controlling the functions of the components of the front portion assembly.

The end effector 120 may be adapted for capturing and transecting tissue and for contemporaneously welding the captured tissue with controlled application of energy (e.g., RF energy). The first jaw 123a and the second jaw 123b may be closed thereby capturing or engaging tissue. The first jaw 123a and second jaw 123b may also apply compression to the tissue. In some aspects, the shaft 115, along with the first jaw 123a and second jaw 123b, can be rotated a full 360° degrees relative to the jaw closure trigger 127. For example, a rotation knob 117 may be rotatable about the longitudinal axis of the shaft 115 and may be coupled to the shaft 115 such that rotation of the knob 117 causes corresponding rotation of the shaft 115. The first jaw 123a and the second jaw 123b can remain openable and/or closeable while rotated.

The reusable handle assembly 130 may include a reusable handle housing which may, in some non-limiting examples, be formed into a handle 133.

FIG. 1A illustrates an example in which the front portion assembly 110 may be brought into contact with the reusable handle assembly 130 by vertically sliding the front portion assembly against the reusable handle assembly (downward arrow). In another non-limiting example, the front portion assembly 110 may be brought into contact with the reusable handle assembly 130 by horizontally aligning the front portion assembly against the reusable handle assembly. In still another non-limiting example, the front portion assembly 110 may be brought into contact with the reusable handle assembly 130 by twisting the front portion assembly against the reusable handle assembly. It may be understood that alternative means of placing the front portion assembly 110 in contact with the reusable handle assembly 130 may be used. Once the front portion assembly 110 is placed in contact with the reusable handle assembly 130, the two assemblies may be releasably affixed to each other using any means known in the art, such as through the use of one or more latches. Such latches may be placed on the housing of the front portion assembly 110, the housing of the reusable handle assembly 130, or on the housing of each of the assemblies as may be required to form a secure contact.

In one non-limiting example, a secure contact between the front portion assembly 110 and the reusable handle assembly 130 may be made by assuring that the front portion assembly proximal interface end 125 is placed in proper mechanical and electrical contact with the distal interface end of the reusable handle assembly 130. Proper mechanical contact may be understood to mean that the mechanical components of the reusable handle assembly 130 may correctly actuate the mechanical components of the front portion assembly 110 according to the electrosurgical system 100 design. Similarly, proper electrical contact may be understood to mean that the electrical components of the reusable handle assembly 130 are in correct data and electrical communication with the electrical and signal components of the front portion assembly 110 according to the electrosurgical system 100 design. It may be appreciated that such an electrosurgical system 100 may be optimized for single-handed operation.

FIG. 1B illustrates a perspective view of one aspect of an electrosurgical system 100 comprising an assembled device composed of the front portion assembly 110 and the reusable handle assembly 130. FIG. 1B illustrates the relative position of the jaw closure trigger 127 with respect to the handle 133 in the assembled electrosurgical system 100. Particularly, jaw closure trigger 127 may be moved through an arc 135 to bring the jaw closure trigger proximate to the handle 133. Such a motion, for example, may result in the closure of the jaws 123a, 123b thereby securing a tissue placed therebetween.

Also illustrated in FIG. 1B are a knife advancement control 140 and an energy activation control 145 located on the front portion assembly housing. In some non-limiting examples, the knife advancement control 140 and the energy activation control 145 may be depressible buttons positioned to permit a user to control knife advancement or energy activation by the use of one or more fingers. In some non-limiting examples, the knife advancement control 140 and the energy activation control 145 may affect knife advancement or energy activation directly by means of one or more mechanical and/or electrical components disposed solely within the front portion assembly 110. In some non-limiting examples, the knife advancement control 140 and the energy activation control 145 may affect knife advancement or energy activation by means of one or more mechanical and/or electrical components disposed within the front portion assembly 110 in coordination with one or more mechanical and/or electrical components disposed within the disposable handle assembly 130. In one non-limiting example, motions of the knife advancement control 140 and the energy activation control 145 may be sensed by one or more sensors disposed within the reusable handle assembly 130. Such sensors may communicate data to a control device disposed within the reusable handle assembly 130. The control device may, in turn, actuate mechanical and/or electrical components within the reusable handle assembly 130 that couple mechanically and/or electrically with components disposed within the front portion assembly 110 to affect knife advancement and/or energy activation at the end effector 120.

FIG. 1O illustrates a close-up perspective view of one aspect of an electrosurgical system 100 to further illustrate components of the end effector 120. It may be appreciated that the jaws 123a, 123b are configured to hold and compress tissue for an electrosurgical procedure. The tissue held by jaws 123a, 123b may be subjected to an electrical current that may heat the tissue sufficiently to cauterize the tissue. Such electrical current may include RF current. In one non-limiting example, the tissue may comprise a blood vessel that may be sealed by compressing and cauterizing the vessel wall. The electrical current may be delivered to the tissue via one or more energy delivery surfaces 127a, 127b located on an inner surface of each jaw 123a, 123b. Each energy delivery surface, in turn, may be in electrical communication with a current supplying terminal. In one non-limiting example, the first energy delivery surface 127a may receive current through an electrode in electrical communication with a source terminal of a current source. Similarly, the second energy delivery surface 127b may source current through an electrode in electrical communication to a drain or ground terminal of the current source. The electrical current used to cauterize the tissue may be supplied by a source of tissue cauterization power. The source of tissue cauterization power may be independent of the electrosurgical system 100 or may be incorporated in the electrosurgical system. In one non-limiting example, the source of tissue cauterization power may comprise one or more batteries disposed within the electrosurgical device 100, for example within a housing of the reusable handle assembly 130.

Figure 2:
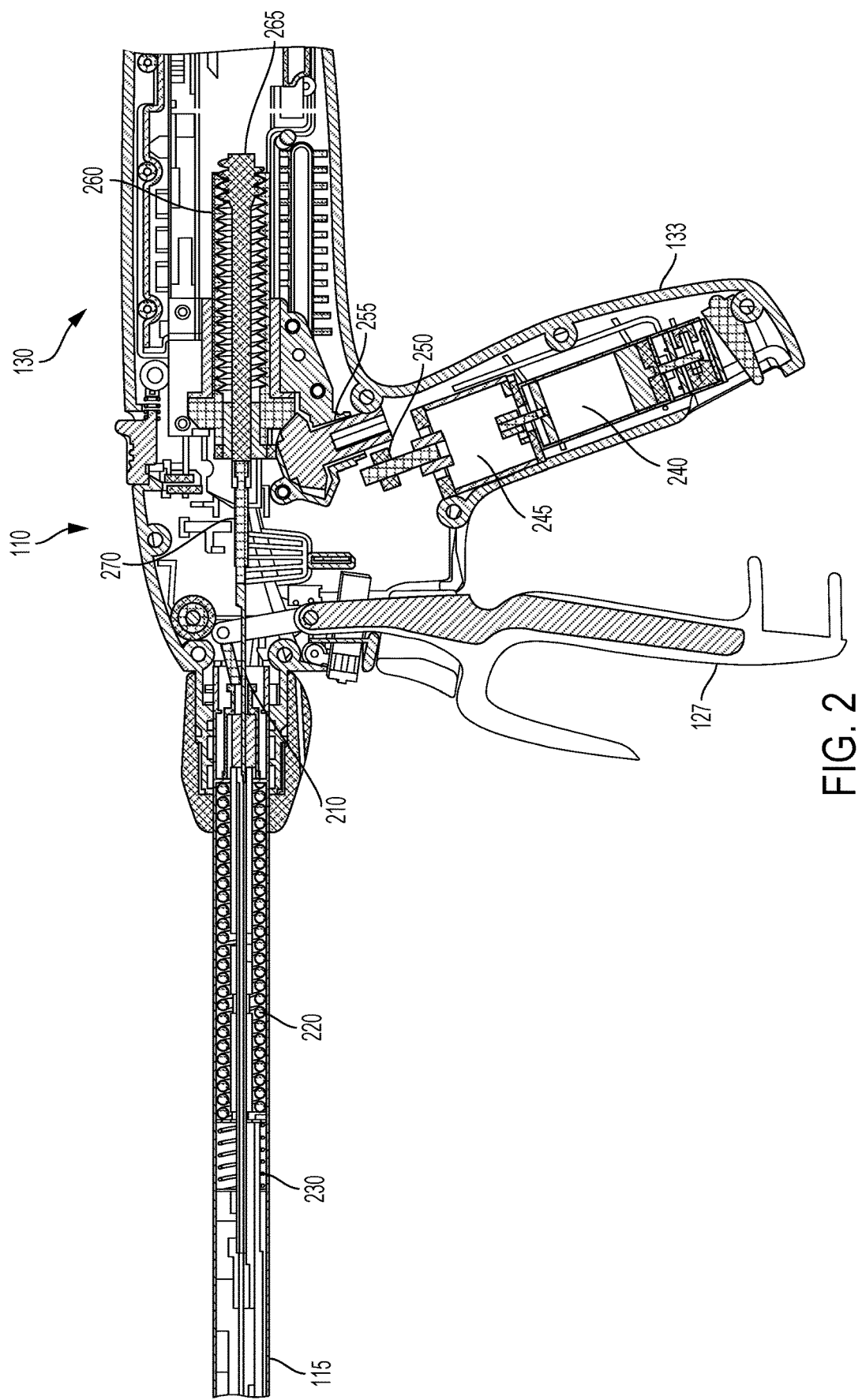
FIG. 2 illustrates a sectional view of one aspect of the electrosurgical device illustrated in FIG. 1B, according to one aspect of the present disclosure.

FIG. 2 illustrates a cross-sectional view of one aspect of an assembled electrosurgical device 100. It may be understood that the components illustrated in FIG. 2, as well as those illustrated in FIGS. 3-6 (following), represent non-limiting examples of mechanical and electromechanical components that may affect the functions of the electrosurgical device 100. Fewer, alternative, or additional components are similarly contemplated by this disclosure.

As disclosed above, the assembled electrosurgical device 100 may be composed of releasably attached portions including a front portion assembly 110 and a reusable handle assembly 130. The front portion assembly 110 may include a shaft 115 in mechanical communication with a front portion assembly housing at a proximal end, and an end effector 120 at a distal end.

The jaw closure trigger 127 may be adapted to actuate an axially moveable member which may function as a jaw-closing mechanism. For example, the axially moveable member may be urged distally as the jaw closure trigger 127 is pulled proximally along the path 135. Such a distal motion of the axially moveable member may be mechanically coupled to a jaw motion assembly to cause the jaws 123a, 1213b to close, thereby contacting and compressing a tissue placed therebetween. The axially moveable member may comprise one or several pieces, but in any event, may be movable or translatable with respect to the shaft 115 and/or the jaws 123a, 123b. The force applied to the axially moveable member via the jaw closure trigger 127 may be controlled or limited by a force limiting spring 230. In addition, the force limiting spring 230 may also protect components from being overloaded when motion of jaws 123a, 123b is restricted due to large amount of tissue. When the jaw closure trigger 127 is returned to a distal position along path 135, the axially moveable member may return to a proximal position, thereby allowing the jaws 123a, 123b to resume an open position and release any tissue compressed therebetween. In some non-limiting examples, the axially moveable member may be returned to its proximal position by means of a return spring 220. The return spring 220 may also act as a force limiting spring that may be used to protect components from being overloaded when the jaw movement is restricted by a large amount of tissue.

In addition to the jaws 123a and 123b, the end effector 120 may also incorporate a tissue knife movably disposed therein. One or both of the jaws 123a, 123b may include a channel disposed on an inner surface. The channels within first jaw 123a and within the second jaw 123b may be sized and configured to accommodate the movement of the tissue knife, which may slidably move within the channels. In at least one example, the tissue knife may be made of 17-4 precipitation hardened stainless steel. The tissue knife may be moved in a distal manner to sever any tissue compressed between the jaws 123a, 123b. The tissue knife may be actuated by means of a knife advancement component 210. The knife advancement component 210 may be an axially moveable component disposed within shaft 115. In one non-limiting example, the knife advancement component 210 may be a rod disposed through shaft 115. In another non-limiting example, the knife advancement component 210 may comprise a tube disposed through shaft 115. A conductor may be disposed inside of a tubular knife advancement component 210 to conduct electrical current from a current supplying terminal to the one or more energy delivery surfaces 127a, 127b located on the inner surface of each jaw 123a, 123b. The knife advancement component 210 may be coupled within the front portion housing to a knife advancement coupling 270. As disclosed below, the knife advancement coupling 270 may form a mechanical interface between the knife advancement component 210 and a helical drive screw 265 disposed within the reusable handle assembly.

The reusable handle assembly 130 may include a reusable handle housing, a portion of which may form the handle 133. The reusable handle housing may enclose one or more mechanical, electromechanical, and electrical components. In aggregate, the mechanical components may be referred to as one or more mechanical couplings which may be designed to couple motions from electromechanical devices in the reusable handle assembly 130 to the mechanical devices disposed in the front portion assembly 110. Some non-limiting examples of such mechanical components may include one or more of a spur gear, a worm gear, a planetary gear set, a helical gear, a bevel gear, a miter gear, and a rack and pinion gear set. Additional non-limiting examples of such mechanical, electromechanical, and electrical components may include a motor 240, one or more gear-sets 245 (for example, a planetary gear set) in mechanical communication with an output shaft of the motor, and one or more additional gears, such as a spur gear 250, that may transfer mechanical motion from the one or more gear-sets to additional mechanical components. The motor 240 may be any type of motor that may provide sufficient torque and speed as may be required for actuation of the mechanical components. Non-limiting examples of such a motor 240 may include a DC motor, an AC motor, and a stepper motor. In one non-limiting example, the motor 240 may receive power from a power source external to the electrosurgical system 100. The handle 133 may also include a mobile power source (such as a battery) that may be used to provide electrical power for the motor 240 and other components of the electrosurgical device.

The handle 133 may also include a controller configured to control the motor 240, receive data from one or more sensors (disclosed below), and/or activate other electromechanical devices disposed within the reusable handle assembly 130. Such a controller may also receive electrical power from a power source such as an external power source or a mobile power source disposed within the reusable handle assembly 130.

In some non-limiting examples, the controller may comprise a processor subsystem, an input/output subsystem, a memory subsystem, a communications interface, and a system bus. In some non-limiting examples, the controller may comprise other components such as an independent power subsystem. In some non-limiting examples, the controller may comprise multiple memory subsystems.

The processor subsystem may comprise any processing circuitry operative to control the operations and performance of the controller. In various aspects, the processor subsystem may be implemented as a general purpose processor, a chip multiprocessor (CMP), a dedicated processor, an embedded processor, a digital signal processor (DSP), a network processor, a media processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIVV) microprocessor, or other processing device. The processor subsystem also may be implemented by a microcontroller, an application specific integrated circuit (ASIC), a field programmable gate array (FPGA), a programmable logic device (PLD), and so forth.

In various non-limiting examples, the processor subsystem may be arranged to run an operating system (OS), preferably a real-time operating system (RTOS). Examples of an OS comprise, for example, operating systems generally known under the trade name of Apple Mac® OS, Microsoft Windows® OS, Android® OS, QNX4®, embedded Linux®, VxWorks®, and any other proprietary or open source OS.

The memory subsystem may comprise any machine-readable or computer-readable media capable of storing data, including both volatile and non-volatile memory. For example, memory may include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

In some aspects, the controller may comprise a system bus that couples various system components including the processing subsystem, the input/output subsystem, and the memory subsystem. The system bus can be any of several types of bus structure(s) including a memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect Card International Association Bus (PCMCIA), Small Computers Interface (SCSI) or other proprietary bus, or any custom bus suitable for mobile computing device applications.

In addition, the controller may include components to receive electrical data from one or more sensors, and/or components to source one or more control signals to one or more electromechanical devices. In one non-limiting example, the controller may include components to receive data from sensors configured to detect to motion or position of the knife advancement control 140 and the energy activation control 145. In another non-limiting example, the controller may include components to source control signals may be used to control the motion of the motor 240. Such motor control signals may include controls of the direction of shaft rotation and the speed of the shaft rotation.

The controller may include instructions resident within components of the memory subsystem that, when active, may cause the processor subsystem to calculate data values and/or control the sourcing of the one or more control signals. In one non-limiting example, the processor subsystem may receive data from a sensor associated with the activation of knife advancement control 140 and calculate if the knife advancement control has been moved to a predetermined position. When the controller determines that the knife advancement control 140 is at the predetermined position, the controller may then source a control signal to the motor 240 to activate a motor motion that may result in motion of the tissue knife. In one non-limiting example, the controller may include fixed instructions and data within the memory subsystem. In another non-limiting example, the controller may be programmable and may receive updated instructions and/or data for storage in the memory subsystem.

In addition to the mechanical, electrical, and/or electromechanical components disposed within the handle 133, the reusable handle assembly 130 may include additional mechanical, electrical, and/or electromechanical components disposed within other portions of the reusable handle housing. In one non-limiting example, additional components may include one or more bevel or miter gears 255 to transfer the rotary force generated by the spur gear 250 to one or more other mechanical devices. For example, the spur gear 250 may be mechanically coupled to a helical drive nut 260. The spur gear 250 may drive bevel gear 255 by means of a second spur gear that is directly coupled to the bevel gear 255 through a shaft attached to the bevel gear. It may be understood that, in another aspect, the bevel gear 255 may be driven directly by the shaft of the motor 240 or by an output shaft of one or more gear-sets 245 mechanically driven by the motor.

Bevel gear 255 may drive a second bevel gear that is part of helical drive nut 260. The bevel gear and helical drive nut 260 may be internally threaded. A helical drive screw 265 has an external threaded component that mates with the internal thread of the helical drive nut 260. Rotation of helical drive nut 260 may transfer motion to the interior helical drive screw 265. The helical drive screw 265, in turn, may advance or return based on the rotational direction of the helical drive nut 260. The helical drive screw 265 may form a contact with knife advancement coupling 270 and impart a motion to the tissue knife at the end effector 120.

Figure 3:
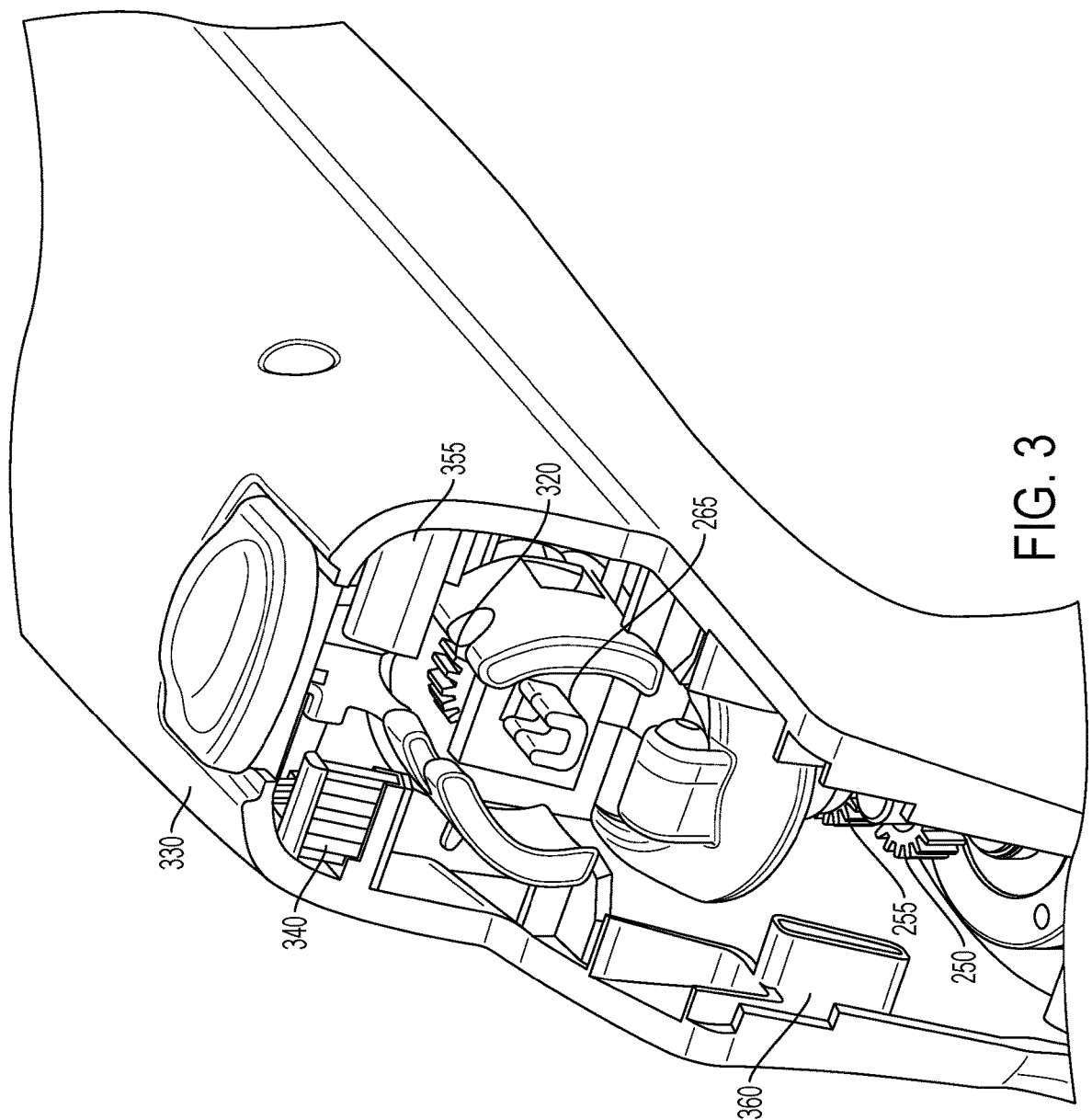
FIG. 3 illustrates a partial cut-away view of one aspect of a reusable handle assembly for an electrosurgical device, according to one aspect of the present disclosure.

FIG. 3 illustrates a partial cut-away view of one aspect of the reusable handle assembly 130. In addition to the spur gear 250, miter gear 255, and helical drive screw 265 depicted in FIG. 2, FIG. 3 illustrates additional components that may be included in the reusable handle assembly 130. One such additional component may be a latch 330 incorporated into the reusable handle housing. Such a latch 330 may be readily manipulated to secure the connection between the front portion assembly 110 and the reusable handle assembly 130.

Additional sensors and electrical contacts are also depicted in FIG. 3. For example, a cauterization actuation sensor 360 may detect the presence or motion of the energy activation control 145. Another sensor may include a knife actuation sensor (not shown) to detect the presence or motion of the knife advancement control 140. In addition, an articulation sensor 355 may detect the presence or motion of an articulation control for an electrosurgical device that has an articulating front end (see FIG. 4, below). It may be understood that sensors 355, and 360 may include, without limitation, one or more of any type of appropriate sensor include a Hall sensor, an RF sensor, a proximity sensor, an inductance sensor, a capacitance sensor, a mechanical sensor, a potentiometer, an optical sensor, and an electronic sensor. One or more tissue cauterization current terminals 340 may be used to conduct tissue cauterization current from a source of tissue cauterization power to the one or more energy deliver surfaces 127*a*, 127*b* incorporated in the inner surfaces of the jaws 123*a*, 123*b*. The front portion assembly 110 may include one or more tissue cauterization power contacts (730, see FIG. 7), wherein the tissue cauterization power contacts are configured to be in electrical communication with equivalent cauterization current terminals 340 from the reusable handle assembly 130.

Additional sensors may include one or more identification sensors configured to receive identification information from an information storage device disposed within the front portion assembly 110. Data information received by any of the sensors, including, without limitation, the cauterization actuation sensor 360, the knife actuation sensor (not shown), an articulation sensor 355, and the one or more identification sensors may be transmitted to the controller. The information storage device may include one or more non-volatile devices, read/write devices, and WORM devices. In some non-limiting examples, the information storage device may include one or more RFID tags, PROM devices, EPROM devices, and EEPROM devices. The information provided by the information storage device may include an identifier of a front portion assembly type (for example, a non-articulated shaft or an articulated shaft), a front portion assembly model number, a front portion assembly serial number, a value of the number of uses of the front portion assembly 110, and a configuration of one or more components of the front portion assembly. In some non-limiting examples, the information storage device may provide its information through a non-contact sensor, for example through an antenna to receive an RF signal from an RFID. In other non-limiting examples, the information storage device may provide its information directly via one or more electrical contacts disposed in the reusable handle assembly distal interface.

As disclosed above, a variety of electrosurgical devices have been developed for use in a variety of procedures. In some procedures, a straight and non-bendable shaft may be used to permit access to some tissues. Alternatively, some tissues may be located in places not readily accessible to a device having a straight and non-bendable shaft. Specific devices may be used that permit a health professional to treat tissue by using an electrosurgical device having a bendable shaft. In one example of such an instrument, the shaft may include one or more articulated joints that may permit the shaft to bend under control by the user. A reusable handle assembly 130, designed for use with both types of devices, may require components configured to active articulation mechanisms that may not exist in front portion assemblies lacking an articulated shaft. Thus, FIG. 3 further illustrates an articulation drive gear 320 that may couple one or more motions of the motor 240 to an articulation mechanism present in a front portion assembly having an articulated shaft.

Figure 4:
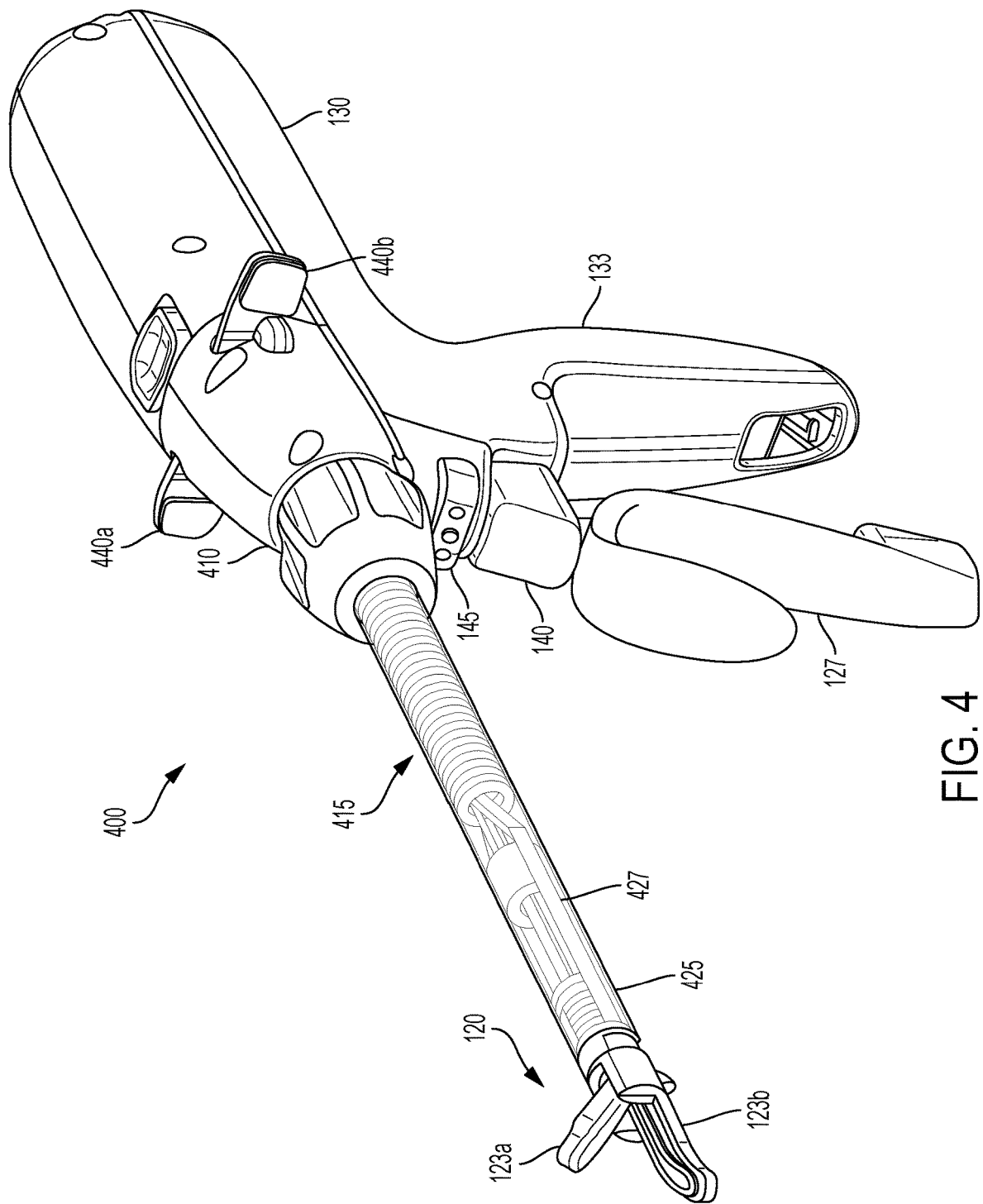
FIG. 4 illustrates a perspective view of one aspect of an electrosurgical device having an articulated shaft, according to one aspect of the present disclosure.

FIG. 4 illustrates one aspect of an electrosurgical device 400 having an articulated shaft 415 as a component of a front portion assembly 410. It may be appreciated that many of the features depicted in FIG. 4 are equivalent to those depicted in FIG. 1B. Thus, the electrosurgical device 400 incorporates a reusable handle assembly 130 having a housing that forms, in part, a handle 133. A jaw closure trigger 127 is incorporated in the front portion assembly 410 as well as a knife advancement control 140 and an energy activation control 145. The end effector 120 additionally is composed of a pair of jaw 123*a*, 123*b*. The articulated shaft 415 extends in a distal direction from the front portion assembly housing and is in mechanical communication with the end effector 120. Although not shown, a tissue knife is disposed within the end effector 120 and is configured to cut tissue that may be compressed and cauterized by the jaws 123*a*, 123*b*.

The articulated shaft 415 incorporates an articulation joint 425. The articulation joint 425 is configured to permit a portion of the shaft 415 distal to the articulation joint to move in a plane orthogonal to a plane of a motion of the first jaw 123a with respect to the second jaw 123b. The articulation joint 425 may be moved by means of an articulation mechanism. The articulation mechanism may include one or more articulation bands 427. The articulation mechanism may be actuated by means of one or more articulation controls, 440a, 440b. In one non-limiting example, a single articulation control (for example 440a) may be included in the front portion assembly 410. In another non-limiting example, each articulation control 440a, 440b may act independently of the other, thereby permitting ambidextrous control of the articulated shaft 415. In yet another non-limiting example, activation of one of the articulation controls (for example 440a) may result in the articulation mechanism bending the articulated shaft 415 in a first direction, while activation of the second articulation control (for example 440b) may result in the articulation mechanism bending the articulated shaft 415 in a second direction.

Figure 5:
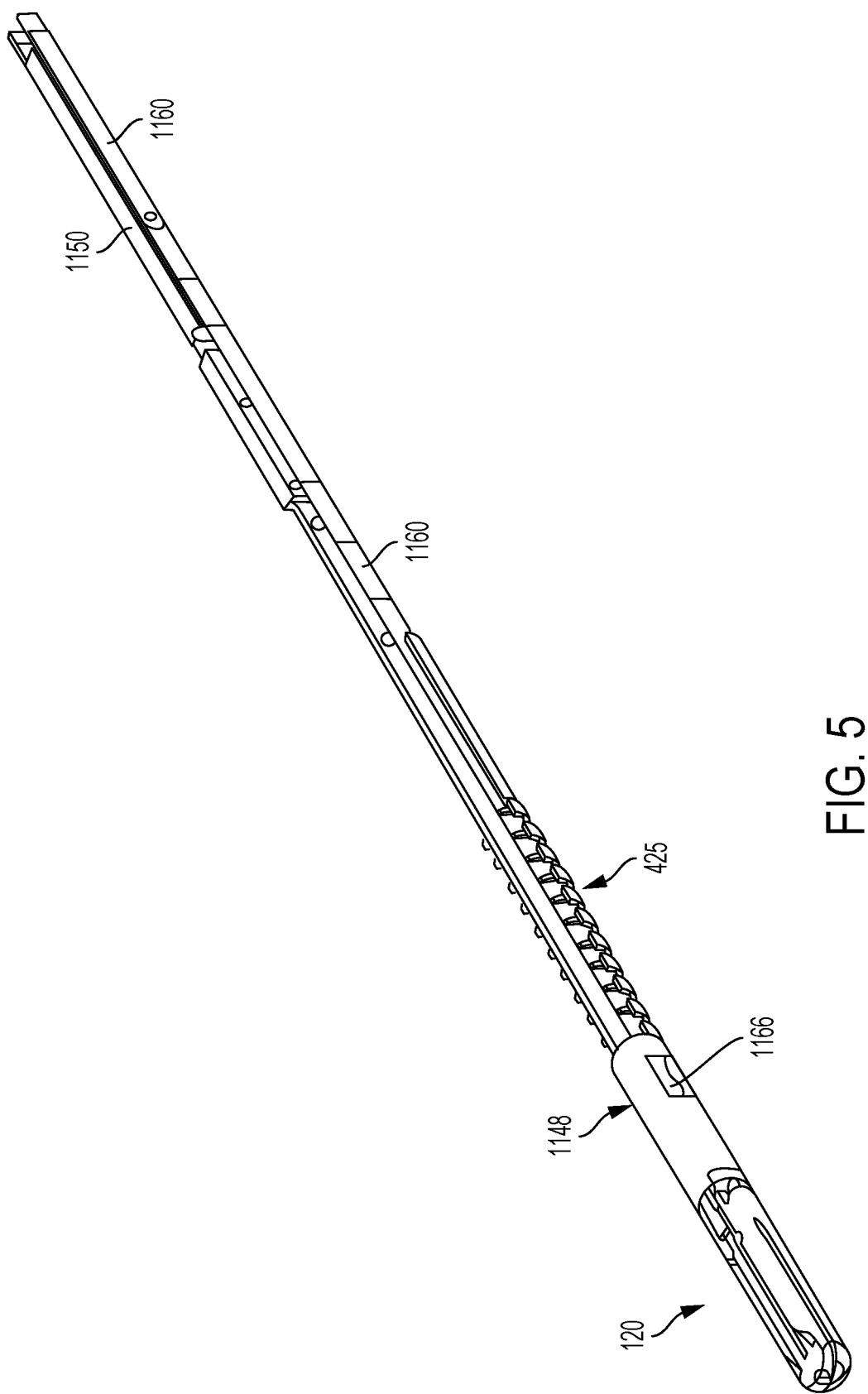
FIG. 5 depicts a perspective view of one aspect of components of the shaft assembly and end effector of the electrosurgical device illustrated in FIG. 4, according to one aspect of the present disclosure.

FIG. 5 depicts one aspect of components of the articulating shaft 415. As shown in FIG. 5, these components include a separator 1150, a first articulation band 1170 (see FIG. 6B) on a first side of the separator and a second articulation band 1160 disposed on a second side and opposing side of the separator. Separator 1150 may include a first side recess along the first side of the separator along which the first articulation band 1170 may travel, and a second side recess along the second side of the separator along which the second articulation band 1160 may travel. Separator 1150 is disposed within the articulated shaft 415 at a fixed longitudinal position during operation of electrosurgical device. Thus, separator 1150 remains stationary relative to the articulated shaft 415. The distal end 1166 of second articulation band 1160 is secured to one side of the proximal portion 1148 of end effector 120 at an anchor point. Similarly, a distal end of a first articulation band 1170 may be secured to the other side of proximal portion 1148 of end effector 120 at an anchor point. As will be described in greater detail below, an articulation control assembly is operable to selectively advance one articulation band distally while simultaneously retracting the other articulation band proximally, and vice-versa. It should be understood that this opposing translation will cause articulation joint 425 to bend, thereby articulating end effector 120. In particular, end effector 120 will deflect toward whichever articulation band is being retracted proximally; and away from whichever articulation band is being advanced distally.

Figure 6A:
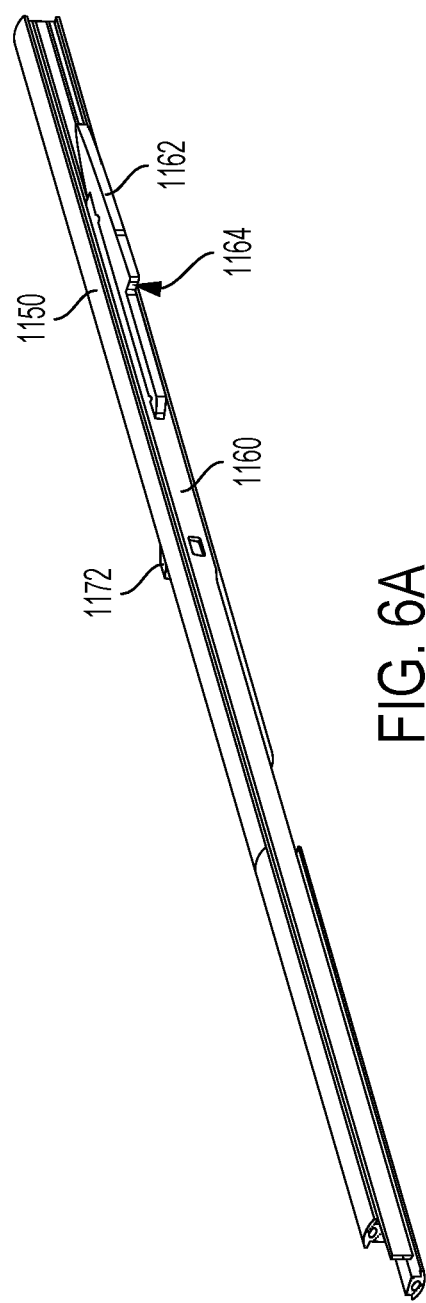
FIGS. 6A and 6B illustrate partial perspective views of one aspect of articulation control components of the electrosurgical device of FIG. 5, along a first side and along a second side of the support member, respectively, according to one aspect of the present disclosure.
Figure 6B:
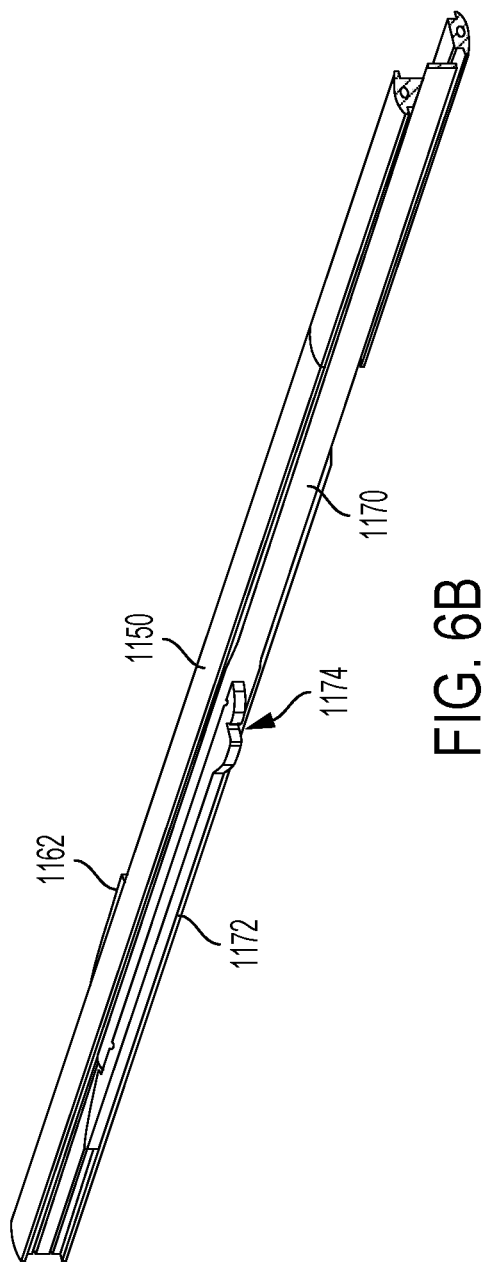

As depicted in FIGS. 6A and 6B, each articulation band has associated with it a drive member configured to move its associated articulation band in a proximal or distal direction relative to the articulation shaft 415. Thus, a first drive member 1172 having a first notch 1174 extending laterally inwardly may be unitarily secured to the first articulation band 1170. Similarly, a second drive member 1162 having a second notch 1164 extending laterally inwardly may be unitarily secured to the second articulation band 1160.

In some aspects, the drive members 1162, 1172 may comprise one or more tubes or half-shafts comprising a lengthwise portion of a tube. Thus, the first drive member 1172 may comprise a first half-shaft, and the second drive member 1162 may comprise a second half-shaft. Each half-shaft may be attached to an articulation band at a first end and an articulation mechanism bushing at a second end. The half-shafts may be configured to surround a tubular knife advancement component 210 thereby allowing the knife advancement component to move axially therebetween. In some aspects, the two half-shafts may be disposed within a second tube configured to actuate jaws 123a, 123b. It may be recognized that such one aspect may comprise nested tubular components configured to allow independent actuation of the jaws 123a, 123b, knife, and articulation joint 425. In another aspect, each drive member 1162,1172, the knife advancement component 210, and one or more members to actuate jaws 123a, 123b may comprise an individually actuated rod disposed axially and parallel to each other within the shaft 115. It may be understood that additional components within the shaft 115 may be disposed to maintain the axial and parallel orientation of such rods and to prevent the rods from interfering with each other upon actuation.

Figure 7:
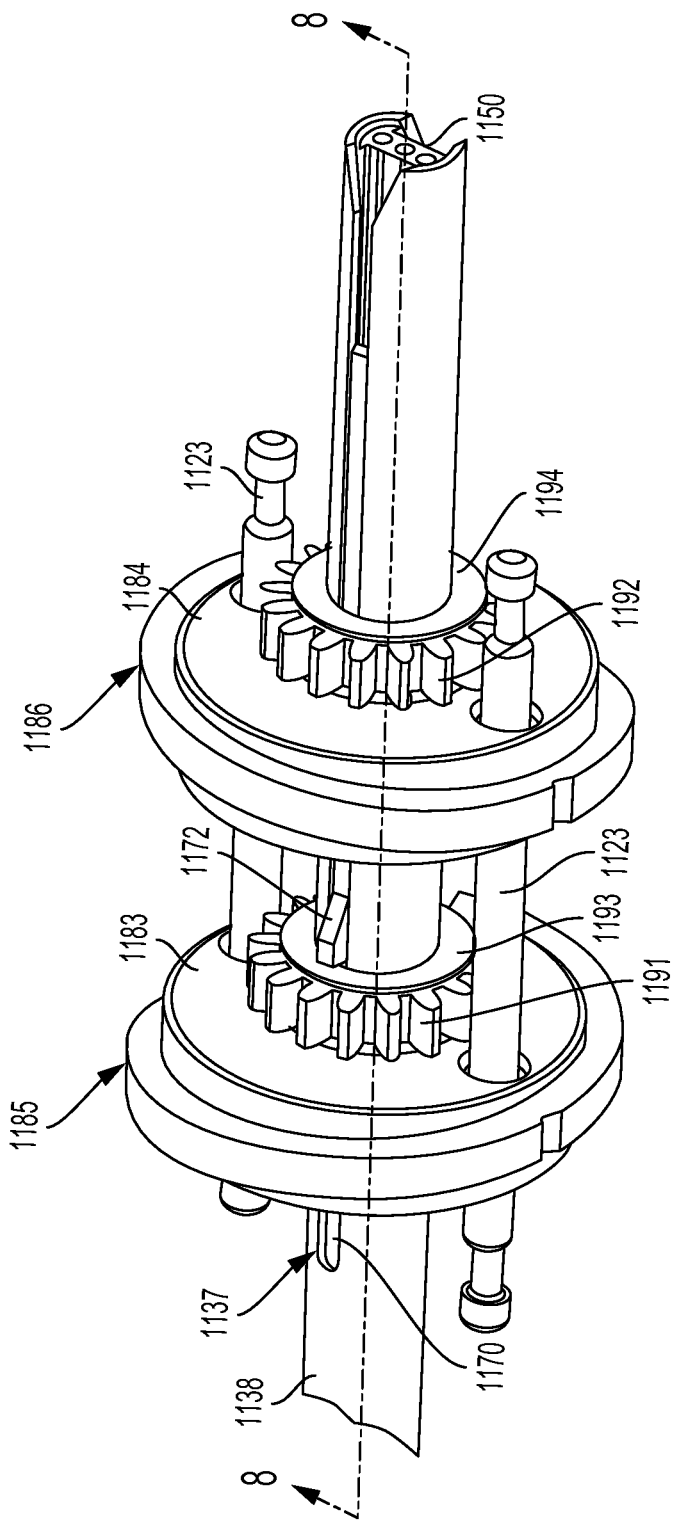
FIG. 7 illustrates a perspective view of one aspect of an articulation control assembly of the front portion assembly of FIG. 4, coupled with the articulation control components of FIGS. 5, 6A and 6B, according to one aspect of the present disclosure.

FIG. 7 depicts one aspect of an articulation control assembly that may be used to manipulate the drive members 1162 and 1172 to move the respective articulation bands 1160 and 1170 in either a proximal or distal direction. As depicted in FIG. 7, articulation control assembly may comprise a first lead screw 1183 and a second lead screw 1184 that are slidably disposed along a pair of pins 1123 within the articulation drive gear 610 (See FIG. 9). Thus, lead screws 1183, 1184 are operable to translate within the articulation drive gear 610 but are prevented from rotating within it. First lead screw 1183 includes exterior threading 1185 that is engaged with a first portion of the internal threading of articulation drive gear 610, and second lead screw 1184 includes exterior threading 1186 that is engaged with a second portion of the internal threading of articulation drive gear 610. It should therefore be understood that, due to the opposing pitch angles, rotation of articulation drive gear 610 in a first direction will drive lead screw 1183 distally while simultaneously driving lead screw 1184 proximally. Similarly, rotation of articulation drive gear 610 in a second direction will drive lead screw 1183 proximally while simultaneously driving lead screw 1184 distally.

The angles of threading 1185, 1186 are also configured such that articulation joint 425 will be effectively locked in any given articulated position, such that transverse loads on end effector 120 will generally not bend articulation joint 425 due to friction between threading 1185, 1186 and the internal threading of the articulation drive gear 610. In other words, articulation joint 425 will only change its configuration when articulation drive gear 610 is rotated. While the angles of threading may substantially prevent bending of articulation joint 425 in response to transverse loads on end effector 120, the angles may still provide ready rotation of articulation drive gear 610 to translate lead screws 1183, 1184. By way of example only, the angles of threading 1185, 1186 may be approximately +1-2 degrees or approximately +1-3 degrees. Other suitable angles will be apparent to those of ordinary skill in the art in view of the teachings herein. It should also be understood that threading 1185, 1186 may have a square or rectangular cross-section or any other suitable configuration.

Figure 8:
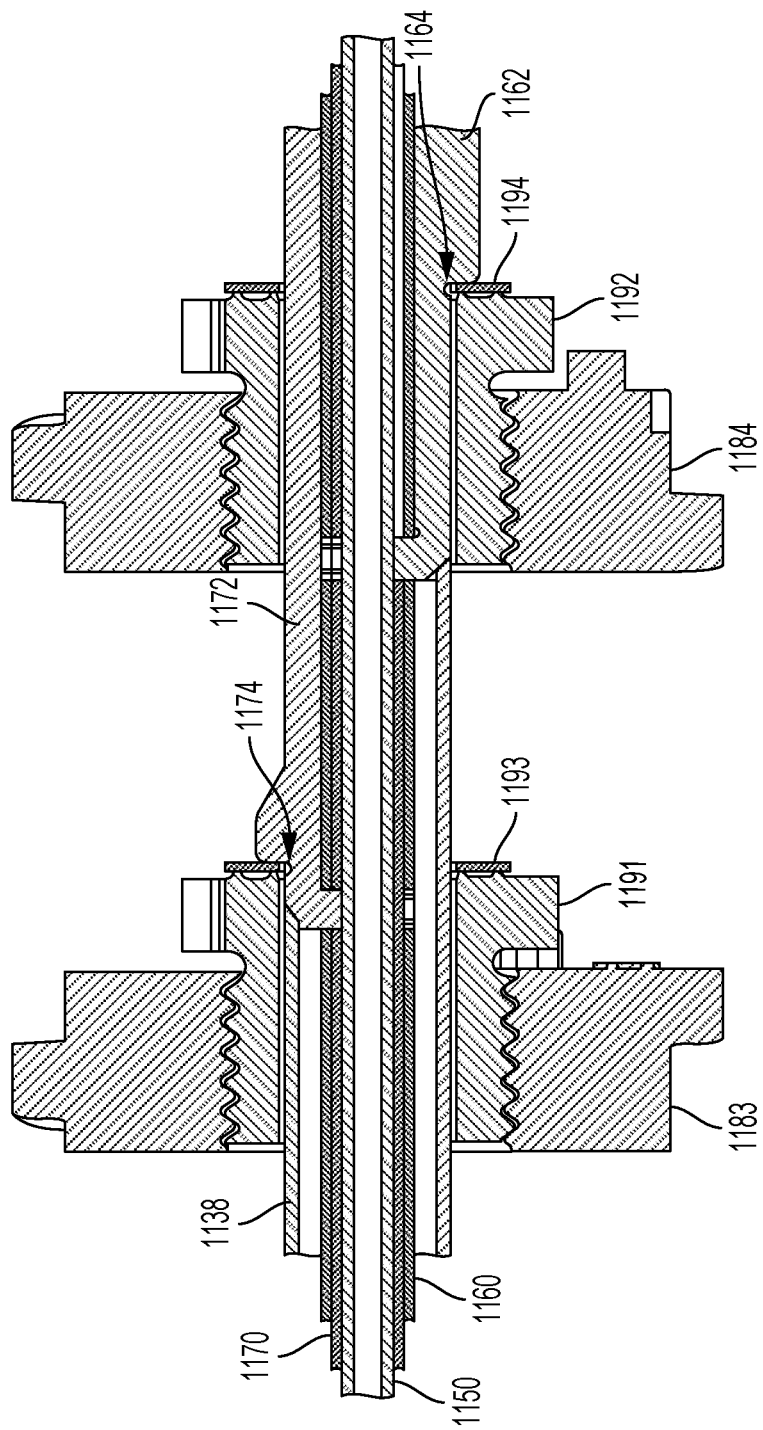
FIG. 8 illustrates depicts a side cross-sectional view of one aspect of the articulation control assembly components of FIG. 7, taken along line 8-8 of FIG. 15, according to one aspect of the present disclosure.

As best seen in FIGS. 7-8, a first tensioner gear 1191 is threadably engaged with first lead screw 1183, while a second tensioner gear 1192 is threadably engaged with second lead screw 1184. Thus, the longitudinal position of first tensioner gear 1191 relative to first lead screw 1183 may be adjusted by rotating first tensioner gear 1191 relative to first lead screw 1183, while the longitudinal position of second tensioner gear 1192 relative to second lead screw 1184 may be adjusted by rotating second tensioner gear 1192 relative to second lead screw 1184. Otherwise, first tensioner gear 1191 will translate unitarily with first lead screw 1183, while second tensioner gear 1192 will translate unitarily with second lead screw 1184.

First tensioner gear 1191 is also engaged with a first washer 1193, which is further engaged with notch 1174 of first drive member 1172. The engagement between first washer 1193 and first drive member 1172 is such that first washer 1193 and first drive member 1172 will translate together. In some versions, first washer 1193 is secured to first tensioner gear 1191 in such a manner that first tensioner gear 1191 both pulls first washer 1193 distally and pushes first washer 1193 proximally. Thus, in some such versions, first lead screw 1183 is operable to both push first articulation band 1170 distally and pull first articulation band 1170 proximally, depending on which direction articulation drive gear 610 is rotated. In the present example, however, first tensioner gear 1191 merely abuts first washer 1193, such that first tensioner gear 1191 is operable to push first washer 1193 proximally but cannot pull first washer 1193 distally. Thus, in the present example, first lead screw 1183 is operable to pull first articulation band 1170 proximally but cannot actively push first articulation band 1170 distally. Instead, first lead screw 1183 may simply pull first tensioner gear 1191 distally to enable first articulation band 1170, first drive member 1172, and first washer 1193 to be driven distally in response to proximal retraction of second articulation band 1160 as communicated through articulation joint 425. Other suitable relationships will be apparent to those of ordinary skill in the art in view of the teachings herein. It should also be understood that first drive member 1172 and/or first washer 1193 may be rotatable relative to first tensioner gear 1191. As described in greater detail below, first tensioner gear 1191 may be used to take out any tolerance gaps between first drive member 1172 and first lead screw 1183.

Similarly, second tensioner gear 1192 is engaged with second washer 1194, which is further engaged with second notch 1164 of second drive member 1162. The engagement between second washer 1194 and second drive member 1162 is such that second washer 1194 and second drive member 1162 will translate together. In some versions, second washer 1194 is secured to second tensioner gear 1192 in such a manner that second tensioner gear 1192 both pulls second washer 1194 distally and pushes second washer 1194 proximally. Thus, in some such versions, second lead screw 1184 is operable to both push second articulation band 1160 distally and pull second articulation band 1160 proximally, depending on which direction articulation drive gear 610 is rotated. In the present example however, second tensioner gear 1192 merely abuts second washer 1194, such that second tensioner gear 1192 is operable to push second washer 1194 proximally but cannot pull second washer 1194 distally. Thus, in the present example, second lead screw 1184 is operable to pull second articulation band 1160 proximally but cannot actively push second articulation band 1160 distally. Instead, second lead screw 1184 may simply pull second tensioner gear 1192 distally to enable second articulation band 1160, second drive member 1162, and second washer 1194 to be driven distally in response to proximal retraction of first articulation band 1170 as communicated through articulation joint 425. Other suitable relationships will be apparent to those of ordinary skill in the art in view of the teachings herein. It should also be understood that second drive member 1162 and/or second washer 1194 may be rotatable relative to second tensioner gear 1192. As described in greater detail below, second tensioner gear 1192 may be used to take out any tolerance gaps between second drive member 1162 and second lead screw 1184.

Figure 9:
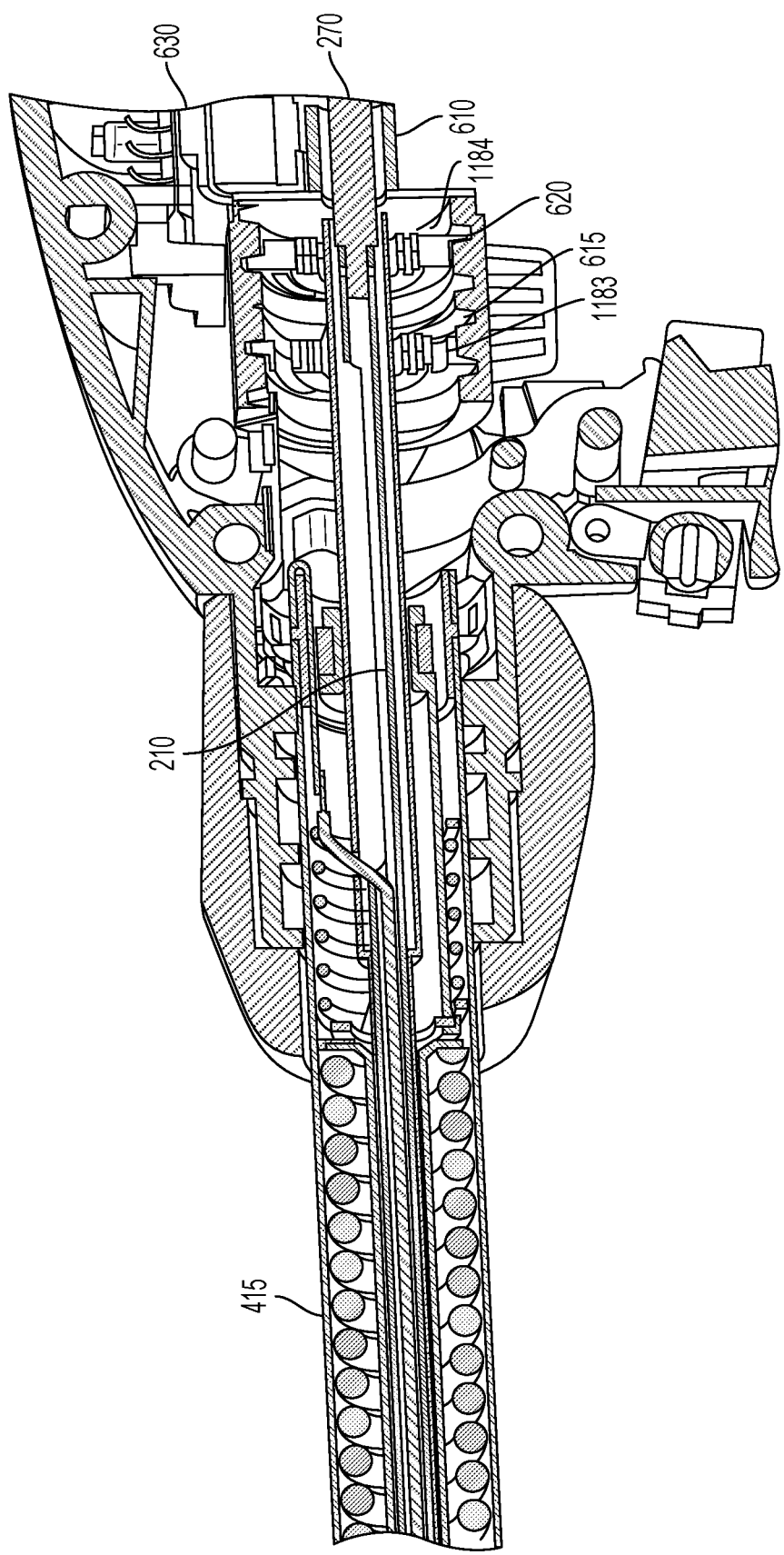
FIG. 9 illustrates a partial sectional view of one aspect of the front portion housing of the electrosurgical device illustrated in FIG. 4, according to one aspect of the present disclosure.

FIG. 9 depicts a close-up view of a section of the front portion assembly 410 including the articulating shaft 415 and an articulation drive assembly. As shown in FIG. 9, articulation drive gear 610 may be coaxially positioned about the proximal portion of knife advancement coupling 270 and may encompass drive members 1162, 1172. Articulation drive gear 610 may be rotatable about the longitudinal axis defined by shaft 415. As will be described in greater detail below, such rotation of articulation drive gear 610 may cause opposing translation of drive members 1162, 1172, with the directions of such opposing translations depending on the direction in which articulation drive gear 610 rotates. In such a manner, rotation of articulation drive gear 610 may articulate end effector 120 about articulation joint 425. Articulation drive gear 610 may include a first internal threading 615 and a second internal threading 620. Threadings 615, 620 may have opposing pitch angles or orientations and may be configured to mate with the exterior threadings 1185 and 1186 of lead screws 1183 and 1184, respectively. Thus, a rotation of articulation drive gear 610 in a first direction may cause first lead screw 1183 to move distally and second lead screw 1184 to move proximally. The distal motion of first lead screw 1183 may cause first drive member 1172 to move distally, while the proximal motion of second lead screw 1184 may cause second drive member 1162 to move in a proximal direction. The resulting push-pull motion of drive members 1172 and 1162, respectively, may result in the bending of the articulation joint 425 to bend in a first direction. Similarly, a rotation of articulation drive gear 610 in a second direction may cause first lead screw 1183 to move proximally and second lead screw 1184 to move distally. The proximal motion of first lead screw 1183 may cause first drive member 1172 to move proximally, while the distal motion of second lead screw 1184 may cause second drive member 1162 to move in a distal direction. The resulting pull-push motion of drive members 1172 and 1162, respectively, may result in the bending of the articulation joint 425 to bend in a second direction. Rotation of the articulation drive gear 610 may be driven by rotation of an articulation coupling gear 630.

Figure 10A:
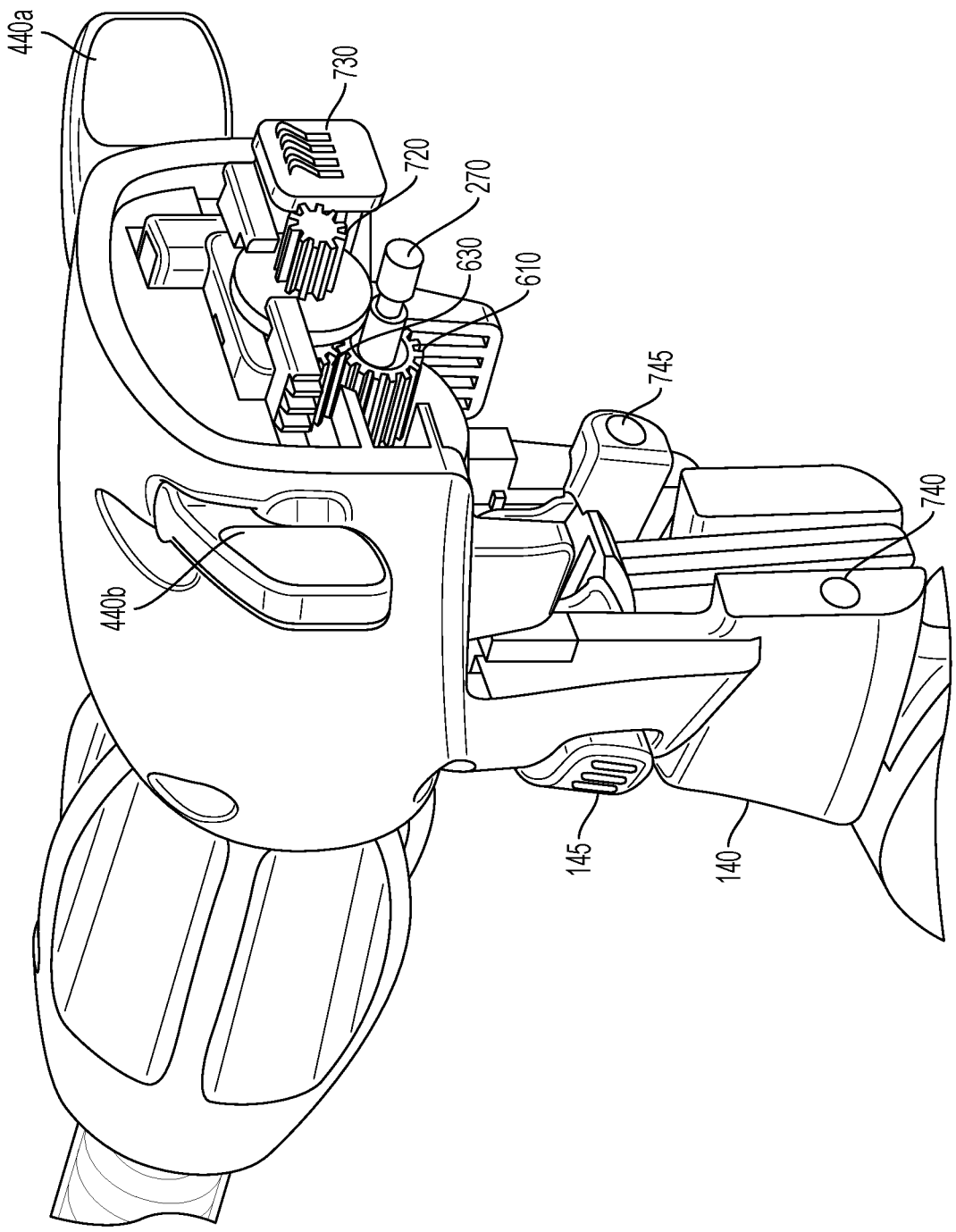
FIG. 10A illustrates a perspective view of a proximal end of the front portion housing of one aspect of the electrosurgical device illustrated in FIG. 4, according to one aspect of the present disclosure.

FIG. 10A depicts an example of a proximal interface of a front portion assembly of an electrosurgical device that incorporates an articulated shaft. Many of the components illustrated in FIG. 10A are common to electrosurgical devices that incorporate a fixed shaft. For example, FIG. 10A illustrates the proximal end of the knife advancement coupling 270. Additionally, FIG. 10A illustrates common controls such as the knife advancement control 140 and the energy activation control 145. As noted above, the reusable handle assembly 130 may include sensors to detect motions of knife advancement control 140 and the energy activation control 145. In a non-limiting example, a cauterization actuation sensor 360 may detect the presence or motion of the energy activation control 145, and a knife actuation sensor (not shown) may detect the presence or motion of the knife advancement control 140. In some non-limiting examples, the cauterization actuation sensor 360 and the knife actuation sensor (not shown) may comprise Hall sensors that may sense the proximity of a magnet 745 associated with the energy activation control 145, and a magnet 740 associated with the knife advancement control 140, respectively. The proximal interface illustrated in FIG. 10A also depicts one or more tissue cauterization power contacts 730 which may be configured to be in electrical communication with equivalent cauterization current terminals 340 (see FIG. 3) in the reusable handle assembly 130.

FIGS. 10A and 10B together disclose one aspect of a mechanism for adjusting an articulation angle in an articulation shaft. Articulation drive gear 610 may be mechanically coupled to articulation coupling gear 630. Articulation coupling gear 630 may be reversibly coupled to an articulation engagement gear 720 using mechanical components attached to the articulation controls 440a, 440b as depicted in FIG. 10B. Manipulation or position of the articulation controls, 440a, 440b, may be sensed by one or more articulation actuation sensors (FIG. 10B, 355a, 355b). In one non-limiting example, the articulation actuation sensors 355a, 355b may comprise Hall sensors that can sense the proximity of articulation magnets 750a, 750b, respectively. Articulation magnets 750a, 750b may be affixed to the mechanical components of the articulation controls 440a, 440b, respectively. Motion of the articulation controls 440a, 440b in direction A, A' (FIG. 10B) may simultaneously cause articulation magnets 750a, 750b to move proximate to the articulation actuation sensors 355a, 355b as well as cause the articulation engagement gear 720 to mechanically couple with articulation drive gear 320. Bias spring 760, co-axial with a shaft of the articulation engagement gear 720, may provide a restoring force that can disengage the articulation engagement gear 720 from the articulation drive gear 320 when pressure to articulation controls 440a or 440b is released. The bias spring 760 may also cause the articulation magnets 750a, 750b to move away from the articulation actuation sensors 355a, 355b when pressure is released from the articulation controls 440a, 440b.

In practice, an electrosurgical system comprising separable front portion assemblies and reusable handle assemblies as disclosed above may be used as follows. The front portion assembly having a front portion housing may be contacted with the reusable handle assembly having a reusable handle housing, and the front portion housing may be releasably latched to the reusable handle housing. Upon contacting the front portion housing with the reusable handle housing, mechanical, electrical, and data components of the front portion assembly may be contacted with mating mechanical, electrical, and data components of the reusable handle housing. The mechanical components of the front portion assembly may include, without limitation, mechanical components to actuate a tissue cutting knife and mechanical components to cause a portion of the front portion assembly shaft to bend about an articulation joint. Electrical components of the front portion assembly may include, without limitation, contacts to transfer an electrical current from a current source in the reusable handle housing to one or more energy delivery surfaces associated with one or more jaws at the distal end of the front portion assembly shaft. In one non-limiting example, a data component may include one or more information storage devices to provide data to or receive data from the controller in the reusable handle assembly. Such information storage devices may be active or passive, and may be read-only or read/write devices.

Upon securing the front portion assembly to the reusable handle assembly, a data storage device in the front portion assembly may provide data to the reusable handle assembly. Such data may include, without limitation, data identifying a type of front portion assembly, data indicating types of mechanical functions available to the front portion assembly, data indicating prior use of the front portion assembly, data indicating the number of times the front portion assembly may be used, data giving an expiration date for use of the front portion assembly, and data indicating limitations of electrical current that may be sourced to the front portion assembly. Identification data may include, without limitation, a part number identifier and a serial number identifier. Mechanical functionality data may include, without limitation, indications that the front portion assembly includes an articulation joint and control interfaces therefor, indications regarding limitations on the angle and distance that the jaws may move, and indications on the length that a tissue cutting knife may move. The information in the data storage device may be altered by the reusable handle assembly upon use of the front portion assembly to track the number of uses of the front portion assembly during one or more surgical procedures. In some non-limiting examples, the reusable handle assembly may receive use data from the data storage device and determine that the front portion assembly may not be useable for additional procedures due to prior use. In another non-limiting example, the reusable handle assembly may receive expiration date data from the data storage device and determine that the front portion assembly may not be useable because the front portion assembly is beyond its expiration date.

Once the front portion assembly and the reusable handle assembly are releasably secured together, the controller in the reusable handle assembly may determine if the two assemblies are properly secured together to allow use. In one non-limiting example, the controller may prevent any subsequent action of the assembled electrosurgical device if it determines that the front portion assembly and the reusable handle assembly are not properly secured together.

The jaw closure trigger of the assembled electrosurgical device may be moved thereby causing the first jaw to move relative to the second jaw thereby capturing a tissue therebetween. The energy activation control may be manipulated, and its motion may be sensed by the cauterization activation sensor. The cauterization activation sensor may transmit a signal to the controller in response to an activation of the energy activation control. In one non-limiting example, the cauterization activation sensor may be a Hall sensor which may detect a magnetic field of a magnet incorporated in the energy activation control when the energy activation control is manipulated. Upon receiving an appropriate signal from the cauterization activation sensor, the controller may cause an RF current to flow between a first RF current terminal and a second RF current terminal when the controller determines that the energy activation control is at least at a predetermined position. The RF current may be sourced to one or more tissue cauterization power contacts in the reusable handle assembly which may conduct the RF current through mating tissue cauterization current terminals in the front portion assembly. The RF current may then be conducted through one or more conductors to the energy delivery surfaces on the jaws of the front portion assembly. In some non-limiting examples, the controller may supply the RF current only while the energy activation control is placed in an activating position by the user. In some alternative non-limiting examples, the controller may supply the RF current for a predetermined period of time once the energy activation control is placed in an activing position. In yet another non-limiting example, the controller may receive data related to the position of the jaws and prevent the RF current from being supplied to the to the one or more tissue cauterization power contacts if the jaws are not in a closed position.

The knife advancement control may be manipulated, and its motion may be sensed by the knife actuation sensor. The knife actuation sensor may transmit a signal to the controller in response to an activation of the knife advancement control. In one non-limiting example, the knife actuation sensor may be a Hall sensor which may detect a magnetic field of a magnet incorporated in the knife advancement control when the knife advancement control is manipulated. Upon receiving an appropriate signal from the knife actuation sensor, the controller may transmit a signal to cause a rotation of the motor to be coupled to the tissue knife advancement component when the position of the knife advancement control is at least at a predetermined position. In one non-limiting example, the knife advancement control may comprise a toggle switch. A single activation of such a toggle switch may signal the controller to activate instructions that may cause the tissue knife to extend and retract in one continuous motion. In an alternative example, the knife advancement control may comprise a push-button. Activation of such a push-button switch may signal the controller to activate instructions that may cause the tissue knife to extend and retract only while the button is pressed.

In another non-limiting example, the helical drive screw, knife advancement coupling, and/or knife advancement component may be sized to provide overtravel of the tissue cutting knife. In such one aspect, activation of the knife advancement control may result in a linear motion of the tissue cutting knife that may not, at least in part, engage the tissue. Thus, for a knife retracted to its full proximal position, the overtravel may result in the tissue cutting knife not engaging any tissue at least during an initial motion of the knife in the distal direction. Tissue engagement, leading to subsequent severing of the tissue, may occur as the tissue cutting knife advances after this initial motion of the tissue cutting knife. In some non-limiting examples, the pitch of the helical drive nut may be non-uniform. As a result, a length of travel of the tissue cutting knife may be less per rotation of the helical drive nut while the knife advancement coupling is at a proximal location than when the knife advancement coupling is at a more distal location.

The controller may determine that the front portion assembly has a shaft incorporating an articulation joint based on data received from the one or more information storage devices in the front portion assembly. Upon such a determination, the controller may accept data from the one or more articulation sensors. The one or more articulation sensors may transmit one or more signals to the controller in response to an activation of the one or more articulation controls. In one non-limiting example, the one or more articulation sensors may be Hall sensors that may detect a magnetic field of a magnet incorporated into the articulation controls when the articulation controls are manipulated. If the controller determines that a position of the one or more articulation controls is at least at a predetermined position, the controller may activate one or more mechanical and/or electromechanical components to cause the articulation mechanism to move, thereby bending the shaft at the articulation joint.

In one non-limiting example, when an articulation control is positioned forward by an operator, an articulation engagement gear may be translated proximally thereby engaging it with an articulation drive gear. Upon receiving a signal from the one or more articulation sensors, the controller may provide instructions to the motor to rotate. Rotation of the motor may be coupled through one or more miter gears or spur gears to the articulation drive gear. The mechanical coupling of the articulation drive gear with the articulation engagement gear, via the articulation control, may result in the rotation of the motor shaft being coupled to the articulation drive gear. Rotation of the articulation drive gear may result in translation motions of the first and second lead screws which may result in relative translation of the first and second drive members thereby causing the shaft to bend at the articulation joint.

In one non-limiting example, the articulation control may act as a push-button switch. Activation of such a push-button switch may signal the controller to activate instructions that may result in the articulation joint moving first in one direction and then in the opposite direction in one continuous motion only while the button is pressed. In an alternative example, the articulation control may comprise a double-pole switch. Activation of such a double-pole switch may signal the controller to activate instructions that may result in the articulation joint bending in a first direction while the switch contacts a first pole, and may result in the articulation joint bending in a second direction while the switch contacts a second pole. In yet another example, the activation of a first articulation control may signal the controller to move the articulation joint in a first direction, while the activation of a second articulation control may signal the controller to move the articulation joint in a second direction. In some non-limiting examples, the controller may also retain information related to the angle formed by the articulation joint.

In one non-limiting example, a single motor may be used to advance the tissue cutting knife and bend the articulation joint. In a non-limiting example, the tissue cutting knife and the articulation joint may both move when the one or more articulation controls is actuated. In such an example, overtravel may be provided for the motion of the tissue cutting knife so that the knife may advance in a distal direction but not engage tissue while the articulation joint moves. Alternatively, the pitch of the helical drive screw may be non-uniform, so that the tissue cutting knife initially advances to a smaller extent while the shaft articulates than when the articulation control is not actuated and the knife has advanced past a predetermined distal position.

It may be recognized that an alternative aspect of the electrosurgical device may include separate motors to move the tissue cutting knife and articulate the shaft at the articulation joint. In yet another alternative aspect, a single motor may actuate the tissue cutting knife and the articulation joint, but the motions of the knife and the joint may be independent. In such an alternative aspect, actuation of the one or more articulation controls may couple only the articulation mechanisms to the motor while preventing the knife advancement mechanisms from engaging the motor. Similarly, actuation of the knife advancement control may couple only the knife advancement mechanisms to the motor while preventing the articulation mechanisms from engaging the motor.

Additional details regarding electrosurgical end effectors, jaw closing mechanisms, and electrosurgical energy delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,112; and U.S. Pat. App. Pub. Nos. 2010/0036370 and 2009/0076506, all of which are incorporated herein by reference in their entirety and made part of this specification.

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," or "down" may be used herein with respect to the illustrated aspects. However, surgical instruments may be used in many orientations and positions, and these terms are not intended to be limiting or absolute.

Various aspects of surgical instruments and robotic surgical systems are described herein. It will be understood by those skilled in the art that the various aspects described herein may be used with the described surgical instruments and robotic surgical systems. The descriptions are provided for example only, and those skilled in the art will understand that the disclosed aspects are not limited to only the devices disclosed herein, but may be used with any compatible surgical instrument or robotic surgical system.

Reference throughout the specification to "various aspects," "some aspects," "one example," or "one aspect" means that a particular feature, structure, or characteristic described in connection with one aspect is included in at least one example. Thus, appearances of the phrases "in various aspects," "in some aspects," "in one example," or "in one aspect" in places throughout the specification are not necessarily all referring to the same aspect. Furthermore, the particular features, structures, or characteristics illustrated or described in connection with one example may be combined, in whole or in part, with features, structures, or characteristics of one or more other aspects without limitation.

While various aspects herein have been illustrated by description of several aspects and while the illustrative aspects have been described in considerable detail, it is not the intention of the applicant to restrict or in any way limit the scope of the appended claims to such detail. Additional advantages and modifications may readily appear to those skilled in the art. As disclosed herein, the present disclosure has been discussed in terms of endoscopic procedures and apparatus. However, use herein of terms such as "endoscopic", should not be construed to limit the present disclosure to an instrument for use only in conjunction with an endoscopic tube (e.g., trocar). On the contrary, it is believed that the present disclosure may find use in any procedure where access is limited to a small incision, including but not limited to laparoscopic procedures, as well as open procedures and natural orifice procedures, such as a transvaginal hysterectomy.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several aspects have been described, it should be apparent, however, that various modifications, alterations and adaptations to those aspects may occur to persons skilled in the art with the attainment of some or all of the advantages of the disclosure. For example, according to various aspects, a single component may be replaced by multiple components, and multiple components may be replaced by a single component, to perform a given function or functions. This application is therefore intended to cover all such modifications, alterations and adaptations without departing from the scope of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered clauses:

Clause 1. A reusable handle for an electrosurgical device, the reusable handle comprising:
 a housing;
 a motor disposed within the housing;
 a controller configured to actuate the motor;
 an electrical interface portion configured to interface with a front portion of the electrosurgical device comprising:
  a plurality of sensors comprising at least a knife actuation sensor, a cauterization actuation sensor, and an articulation actuation sensor, wherein each of the plurality of sensors is in data communication with the controller, and
  at least one tissue cauterization current terminal;
 a mechanical interface portion configured to interface with the front portion of the electrosurgical device comprising:
  a first mechanical coupling configured to couple one or more motions of the motor to a tissue cutting mechanism,
  a second mechanical coupling configured to couple the one or more motions of the motor to an articulation mechanism, and
  a latching mechanism configured to releasably latch the front portion of the electrosurgical device to the housing.

Clause 2. The reusable handle of Clause 1, wherein the plurality of sensors comprises one or more of a Hall sensor, an RF sensor, an optical sensor, and an electronic sensor.

Clause 3. The reusable handle of any one of Clauses 1-2, wherein the first mechanical coupling and the second mechanical coupling independently comprise one or more of a spur gear, a worm gear, a planetary gear set, a helical gear, a bevel gear, a miter gear, and a rack and pinion gear set.

Clause 4. The reusable handle of any one of Clauses 1-3, further comprising one or more power sources configured to supply power to the motor and the controller.

Clause 5. The reusable handle of Clause 4, wherein the one or more power sources comprise one or more batteries disposed within the housing.

Clause 6. The reusable handle of any one of Clauses 1-5, further comprising a source of tissue cauterization power in electrical communication with the at least one tissue cauterization power terminal.

Clause 7. The reusable handle of Clause 6, wherein the source of tissue cauterization power comprises one or more batteries disposed within the housing.

Clause 8. The reusable handle of any one of Clauses 1-6, wherein the controller is configured to activate the one or more motions of the motor at least in response to receiving data from one or more of the a plurality of sensors.

Clause 9. The reusable handle of any one of Clauses 1-8, further comprising an identification sensor configured to receive identification information from the front portion of the electrosurgical device.

Clause 10. The reusable handle of any one of Clauses 1-9, wherein the second mechanical coupling is configured to couple the one or more motions of the motor to the articulation mechanism independent of a coupling of the one or more motions of the motor to the tissue cutting mechanism.

Clause 11. An electrosurgical system comprising:
a front portion assembly comprising:
a front portion housing,
an end effector comprising a first jaw movably disposed to contact a second jaw, a first electrode configured to be in electrical communication with a first RF current terminal, and a second electrode configured to be in electrical communication with a second RF current terminal,
a tissue knife movably disposed within the end effector,
a tissue knife advancement component configured to move the tissue knife within the end effector,
a jaw closure trigger,
a knife advancement control,
an energy activation control, and
an elongated shaft having a distal end in mechanical communication with the end effector; and
a reusable handle assembly comprising:
a reusable handle housing;
a motor disposed within the reusable handle housing;
a controller configured to actuate the motor;
an electrical interface portion configured to interface with the front portion assembly comprising:
a knife actuation sensor configured to sense a position of the knife advancement control,
a cauterization actuation sensor configured to sense a position of the energy activation control,
an articulation actuation sensor,
wherein the knife actuation sensor, the cauterization actuation sensor, and the articulation actuation sensor are in data communication with the controller, the first RF current terminal, and the second RF current terminal;
a mechanical interface portion configured to interface with the front portion of the electrosurgical device, the mechanical interface portion comprising:
a first mechanical coupling configured to couple one or more motions of the motor to the tissue knife advancement component,
a second mechanical coupling configured to couple the one or more motions of the motor to an articulation mechanism, and
a latching mechanism configured to releasably latch the front portion housing to the reusable handle housing;
wherein the front portion assembly is releasably attached to the reusable handle assembly.

Clause 12. The electrosurgical system of Clause 11, wherein the knife actuation sensor, the cauterization actuation sensor, and the articulation actuation sensor independently comprise one or more of a Hall sensor, an RF sensor, an optical sensor, and an electronic sensor.

Clause 13. The electrosurgical system of any one of Clauses 11-12, wherein the front portion assembly releasably attached to the reusable handle assembly comprises an electrosurgical system configured for single-handed operation.

Clause 14. The electrosurgical system of any one of Clauses 11-13, further comprising an RF current source in electrical communication with the first RF current terminal and the second RF current terminal.

Clause 15. The electrosurgical system of any one of Clauses 11-14, further comprising:
an information storage device disposed within the front portion assembly; and
an identification sensor disposed within the reusable handle assembly,
wherein the identification sensor is in data communication with the controller, and
wherein the identification sensor is configured to receive information from the information storage device.

Clause 16. The electrosurgical system of Clauses 15, wherein the information storage device comprises one or more of a non-volatile device, a read/write device, and a WORM device.

Clause 17. The electrosurgical system of Clause 15, wherein the information storage device comprises one or more of an RFID tag, a PROM device, an EPROM device, and an EEPROM device.

Clause 18. The electrosurgical system of Clause 15, wherein the information comprises one or more of an identifier of a front portion assembly type, a front portion assembly model number, a front portion assembly serial number, a value of the number of uses of the front portion assembly, and a configuration of one or more components of the front portion assembly.

Clause 19. The electrosurgical system of any one of Clauses 11-18, wherein the front portion assembly further comprises:
an articulation joint in the elongated shaft, wherein the articulation joint is configured to permit the shaft to move in a plane orthogonal to a plane of a motion of the first jaw with respect to the second jaw;
the articulation mechanism, configured to move the articulation joint; and
an articulation control,
wherein the articulation actuation sensor is configured to sense the position of the articulation control.

Clause 20. A method of using an electrosurgical system, the method comprising:
providing a front portion assembly comprising:
a front portion housing,
an end effector comprising a first jaw movably disposed to contact a second jaw, a first electrode configured to be in electrical communication with a first RF current terminal, and a second electrode configured to be in electrical communication with a second RF current terminal,
a tissue knife movably disposed within the end effector,
a tissue knife advancement component configured to move the tissue knife within the end effector,
a jaw closure trigger,
a knife advancement control,
an energy activation control, and
an elongated shaft having a distal end in mechanical communication with the end effector;
providing a reusable handle assembly comprising:
a reusable handle housing;
a motor disposed within the reusable handle housing;
a controller configured to actuate the motor;
an electrical interface portion configured to interface with the front portion assembly comprising:
a knife actuation sensor configured to sense a position of the knife advancement control,
a cauterization actuation sensor configured to sense a position of the energy activation control, an articulation actuation sensor,
wherein the knife actuation sensor, the cauterization actuation sensor, and the articulation actuation sensor are in data communication with the controller,
the first RF current terminal, and
the second RF current terminal;
a mechanical interface portion configured to interface with the front portion of the electrosurgical device, the mechanical interface portion comprising:
a first mechanical coupling configured to couple one or more motions of the motor to the tissue knife advancement component,
a second mechanical coupling configured to couple the one or more motions of the motor to an articulation mechanism, and
a latching mechanism configured to releasably latch the front portion housing to the reusable handle housing;
contacting the front portion assembly with the reusable handle assembly and releasably latching the front portion housing to the reusable handle housing;
using the jaw closure trigger to move the first jaw relative to the second jaw thereby capturing a material therebetween;
moving the energy activation control;
sensing, by the cauterization activation sensor, the position of the energy activation control;
causing an RF current to flow between the first RF current terminal and the second RF current terminal when the position of the energy activation control sensed by the cauterization activation sensor is at least at a predetermined position;
sensing, by the knife actuation sensor, the position of the knife advancement control; and
causing, by the controller, the motor to move the tissue knife advancement component via the first mechanical coupling when the position of the knife advancement control sensed by the knife actuation sensor is at least at a predetermined position.

Clause 21. The method of Clause 20, wherein providing a front portion assembly further comprises providing a front portion assembly comprising:
an articulation joint in the elongated shaft, wherein the articulation joint is configured to permit the shaft to move in a plane orthogonal to a plane of a motion of the first jaw with respect to the second jaw;
the articulation mechanism, configured to move the articulation joint; and
an articulation control;
wherein providing a reusable handle assembly further comprises providing a reusable handle assembly wherein the articulation actuation sensor is configured to sense the position of the articulation control;
sensing, by the articulation actuation sensor, the position of the articulation control; and
causing, by the controller, the motor to move the articulation mechanism via the second mechanical coupling when the position of the articulation control sensed by the articulation actuation sensor is at least at a predetermined position.

What is claimed is:

1. A reusable handle for an electrosurgical device, the reusable handle comprising:
a housing comprising a handle;
a motor disposed within the housing;
a controller configured to actuate the motor;
an electrical interface portion configured to interface with a front portion of the electrosurgical device comprising:
a plurality of electronic sensors comprising at least an electronic knife actuation sensor, an electronic cauterization actuation sensor, and an electronic articulation actuation sensor, wherein each of the plurality of electronic sensors is in data communication with the controller, and
at least one tissue cauterization current terminal;
a mechanical interface portion configured to interface with the front portion of the electrosurgical device comprising:
a first mechanical coupling configured to couple one or more motions of the motor to a tissue cutting mechanism,
a second mechanical coupling configured to couple the one or more motions of the motor to an articulation mechanism, and
a latching mechanism configured to releasably latch the front portion of the electrosurgical device to the housing,
wherein the handle is configured to operate in conjunction with a jaw closure trigger disposed in the releasably latched front portion, and
wherein the electronic knife actuation sensor is configured to electronically detect a motion of a knife advancement control disposed in the releasably latched front portion.

2. The reusable handle of claim 1, wherein the plurality of electronic sensors comprises one or more of a Hall sensor, an RF sensor, an optical sensor, and an electronic sensor.

3. The reusable handle of claim 1, wherein the first mechanical coupling and the second mechanical coupling independently comprise one or more of a spur gear, a worm gear, a planetary gear set, a helical gear, a bevel gear, a miter gear, and a rack and pinion gear set.

4. The reusable handle of claim 1, further comprising one or more power sources configured to supply power to the motor and the controller.

5. The reusable handle of claim 4, wherein the one or more power sources comprise one or more batteries disposed within the housing.

6. The reusable handle of claim 1, further comprising a source of tissue cauterization power in electrical communication with the at least one tissue cauterization current terminal.

7. The reusable handle of claim 6, wherein the source of tissue cauterization power comprises one or more batteries disposed within the housing.

8. The reusable handle of claim 1, wherein the controller is configured to activate the one or more motions of the motor at least in response to receiving data from one or more of the plurality of electronic sensors.

9. The reusable handle of claim 1, further comprising an identification sensor configured to receive identification information from the front portion of the electrosurgical device.

10. The reusable handle of claim 1, wherein the second mechanical coupling is configured to couple the one or more motions of the motor to the articulation mechanism independent of a coupling of the one or more motions of the motor to the tissue cutting mechanism.

* * * * *